United States Patent
Hirata et al.

(10) Patent No.: US 6,796,939 B1
(45) Date of Patent: Sep. 28, 2004

(54) ELECTRONIC ENDOSCOPE

(75) Inventors: Yasuo Hirata, Hachioji (JP); Yutaka Konomura, Tachikawa (JP); Yasundo Tanaka, Urawa (JP); Katsunori Sakiyama, Akiruno (JP)

(73) Assignee: Olympus Corporation (JP)

( * ) Notice: Subject to any disclaimer, the term of this patent is extended or adjusted under 35 U.S.C. 154(b) by 370 days.

(21) Appl. No.: 09/648,026

(22) Filed: Aug. 25, 2000

(30) Foreign Application Priority Data

| Aug. 26, 1999 | (JP) | 11-240065 |
|---|---|---|
| Sep. 6, 1999 | (JP) | 11-252033 |
| Sep. 6, 1999 | (JP) | 11-252034 |
| Jun. 19, 2000 | (JP) | 2000-183405 |

(51) Int. Cl.$^7$ .................................................. A61B 1/05
(52) U.S. Cl. .................. 600/179; 600/109; 600/175; 600/180
(58) Field of Search ............................ 600/109, 110, 600/112, 160, 172, 178, 179, 180, 175; 348/65, 68, 76

(56) References Cited

U.S. PATENT DOCUMENTS

| 4,895,138 A | * | 1/1990 | Yabe | 385/117 |
|---|---|---|---|---|
| 5,929,901 A | | 7/1999 | Adair et al. | 348/76 |
| 6,066,090 A | * | 5/2000 | Yoon | 600/113 |

FOREIGN PATENT DOCUMENTS

| JP | 63-260526 | 10/1988 | |
|---|---|---|---|
| JP | 63-260527 | 10/1988 | |
| JP | 5-176882 | 7/1993 | |
| JP | 5-309069 | * 11/1993 | ............ A61B/1/04 |
| JP | 3007137 | 11/1994 | |
| JP | 7-360 | 1/1995 | |
| JP | 8-117184 | 5/1996 | |

* cited by examiner

Primary Examiner—John P. Leubecker
(74) Attorney, Agent, or Firm—Ostrolenk, Faber, Gerb & Soffen, LLP

(57) ABSTRACT

An electronic endoscope having an illuminating section in which an LED for illumination that emits illuminating light to illuminate an observed site is provided and a C-MOS image sensor which has an image pickup surface on which an optical image is formed and outputs a video signal.

15 Claims, 24 Drawing Sheets

ENDOSCOPE APPARATUS

FIG.6
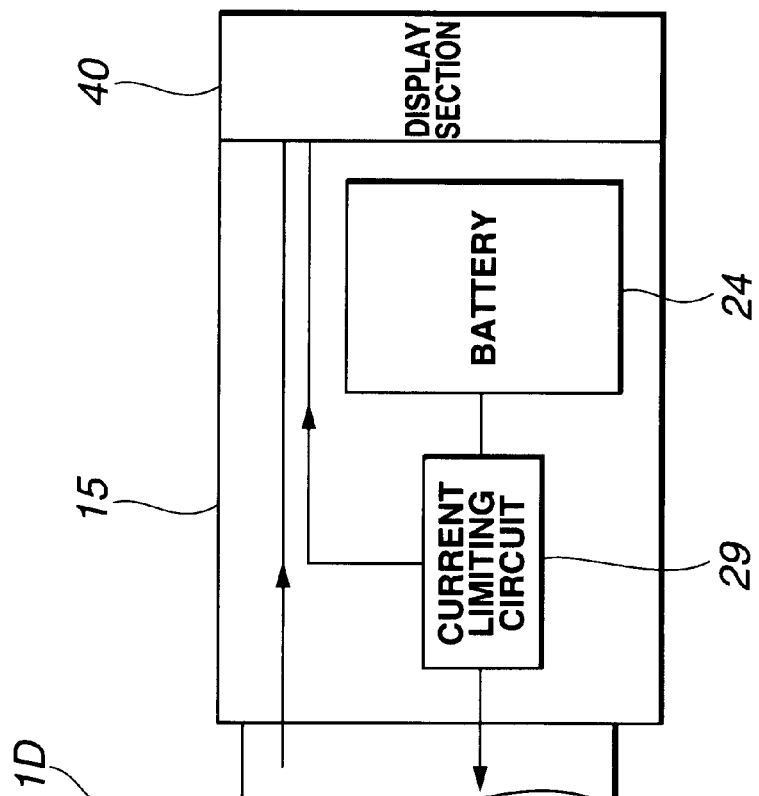
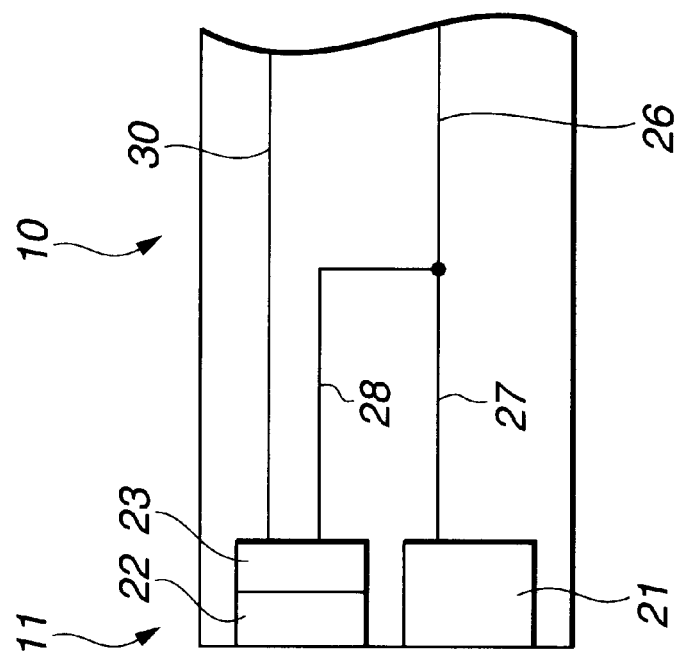

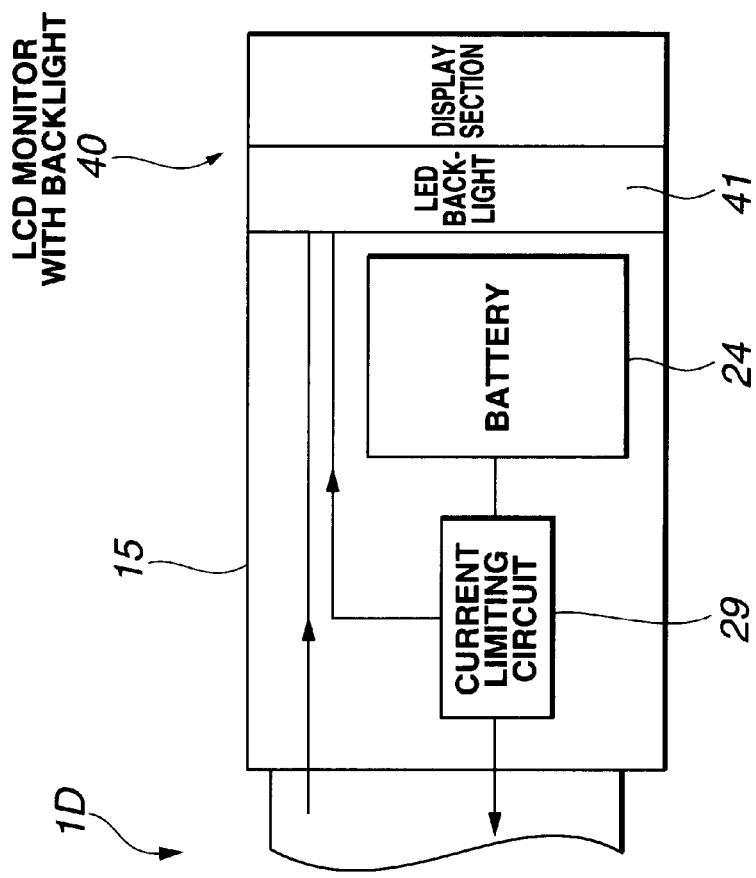
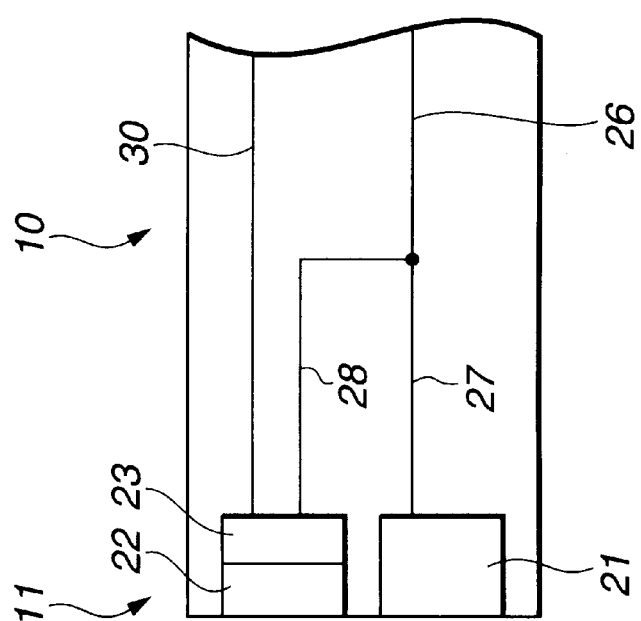
FIG.7

ELECTRONIC ENDOSCOPE

This application claims the benefit of Japanese Application No. Hei 11-240065 filed in Japan on Aug. 26, 1999, Hei 11-252033 filed in Japan on Sep. 6, 1999, Hei 11-252034 filed in Japanese on Sep. 6, 1999, 2000-183405 filed in Japan on Jun. 19, 2000, the contents of which are incorporated herein.

BACKGROUND OF THE INVENTION

1. Field of the Invention

The present invention relates to an electronic endoscope having a C-MOS sensor as an image pickup device and an LED for illumination as illuminating means.

2. Related Art

Recently, there are wide applications of an endoscope whereby the celomic viscera, etc. are observed by inserting an elongated inserting portion in the celom and various treatment can be performed by using a treatment tool which is inserted in a channel of the treatment tool according to the necessity. In the industrial field, an industrial endoscope is also widely used for the observation and the inspection of internal defect and corrosion, etc. of a boiler, turbine, engine, chemical plant, etc.

As the endoscopes which are used as mentioned above, there is an electronic endoscope (abbreviated to an endoscope, hereinafter in which an image pickup device such as a CCD for photoelectrically converting an optical image into an image signal is arranged at the distal end portion of the inserting portion. According to the endoscope, an observed image of an observed site which is illuminated by illuminating light that is supplied from a light source device is formed on an image pickup surface of the CCD. The image signal of the observed image which is obtained by photoelectrically converting by the image pickup device is transmitted to a signal processing section of a camera control unit (abbreviated to a CCU, hereinafter) serving as an external device, a video signal is generated, and an endoscope image is displayed on a screen of a monitor, thereby performing the observation.

In order to provide an endoscope apparatus which is made small in diameter, has simple construction, and realizes various higher functions by eliminating a light guide fiber that is made of an optical fiber, there is disclosed an endoscope apparatus having a solid-state image pickup device for image pickup of an observed site at the distal end portion thereof and a surface light-emitting light source for illuminating the observed site in Japanese Unexamined Patent Application Publication No. 8-117184.

Endoscopes which are used for the industrial are used at dangerous places having explosive atmosphere, etc. such as piping of a chemical plant and a gas tank. The equipment used at the dangerous places needs to satisfy at least a safety standard condition such that "the DC is equal to 28 V or less, the amperage is equal to 93 mA or less, and the wattage is equal to 0.66 W or less," so as to prevent the equipment from becoming an ignition source, etc.

However, the CCDS which are provided in the endoscope have characteristics in that a value of a rising current which is generated in the case of the driving is increased. Therefore, if a problem of a consumption power is solved, the aforementioned condition of the current value is not satisfied, so that a problem remains in the case of the specification which is used at the dangerous places.

The distal end portion has a high temperature due to the heating of electric parts such as a resistor which are provided near the CCDs and the heat of the illuminating light which is supplied from the light source device. There is a problem that the inspection using the electronic endoscope is difficult for pipings, etc. to handle gas which has a danger of firing at a low temperature, e.g., ethyl nitrite whose firing point is 80° C. and ethyl nitrate whose firing point is 85° C.

If a user who operates the endoscope at the dangerous place observes the endoscope image, the display device itself needs to satisfy the safety standard condition. Therefore, it is troublesome to prepare a special display device corresponding to the dangerous places. Further, when a display device of non explosion-proof type is used, inconveniently, the display device is disposed at a safe region and an observer who sees the display device of the non explosion-proof type has to observe the endoscope image or instruct the operator at the dangerous place, etc.

Recently, observed sites become complicated and manifold in accordance with the development of the endoscopic medical science, the medical scene requires an endoscope in which an image pickup device having pixel construction corresponding to the observed site (for example, depending on the pixel size and on the NTSC system or PAL system). There are also a variety of pipings such as pipings as observed targets having a large diameter and a small one and, therefore, the industrial endoscopes also correspond to various inspection by preparing many kinds of optical adapters which are exchangeably mounted to the distal end portion of the endoscope so as to correspond to the variation in the diameter and the inspecting purposes.

However, according to the conventional endoscope apparatuses, a drive circuit and a signal processing circuit of the image pickup device are fixed and, thus, there is a disadvantage that only the endoscope using the image pickup device of the same kind and the same specification can be used. That is, if the endoscope having a different pixel construction of the CCD or the endoscope having a different length of the inserting portion is connected the CCU, a desired endoscope image cannot be displayed on the screen of the monitor from the image signal which is transmitted from the CCD.

In order to solve the disadvantage, according to an endoscope apparatus disclosed in, for instance, Japanese Unexamined Patent Application Publication No. 63-260527, a plurality of CCUs corresponding to different kinds of endoscopes are prepared and the plurality of CCUs are exchangeably mounted in a video process device, thereby enabling different electric scopes to be used. However, the endoscope apparatus cannot be adapted to an existing endoscope apparatus, in other words, an endoscope of a type such that the CCU is not exchangeable in the video process device and the size of video process device is enlarged.

In order to solve the problem, according to an endoscope system disclosed in Japanese Unexamined Patent Application Publication No. 5-176882, a plurality of endoscopes having different kinds of image pickup devices are connected to a CCU corresponding to at least one of the different kinds of image pickup devices and can be used. According to an image pickup system disclosed in Japanese Unexamined Patent Application Publication No. 7-360, one CCU can correspond to a probe having image pickup devices whose image pickup methods are different, thereby reducing costs.

Moreover, in order to prevent the best endoscope image from being displayed by decreasing the length of a signal cable which is inserted in an inserting portion of the endoscope depending on the differences in the length of the inserting portion and the maintenance and adjustment, etc., the CCU is provided with cable length correcting means corresponding to the change in the length of the inserting portion or the cable length.

However, the cable length correcting means is provided, and the endoscope system or the image pickup system corresponds to the difference of the CCD which is provided at the distal end portion thereof as disclosed in Japanese Unexamined Patent Application Publication No. 5-176882 or 7-360, thereby, the construction of the CCU becomes complicated. Not only does the price increase but also the size increases and, thus, cause a serious problem for the industrial endoscopes which require mobility.

OBJECTS AND SUMMARY OF THE INVENTION

It is one object of the present invention to provide an electronic endoscope which has a small consumption of power and satisfies a safety standard condition at dangerous places.

It is another object of the present invention to provide an electronic endoscope which can be handled by a user at dangerous places while observing an endoscope image.

It is yet another object of the present invention to provide an electronic endoscope which is made small in diameter and has high mobility and by which the observation is performed, thereby obtaining an observed image with a preferable picture quality by desired number of pixels and construction in pixel in accordance with an inspecting situation and an inspecting purpose.

Simply speaking, an electronic endoscope of the present invention has an illuminating section which is provided with an LED for illumination that emits illuminating light to illuminate an observed site and a C-MOS image sensor that has an image pickup surface on which an optical image is formed and outputs a video signal and, therefore, has a construction which is suitable to various observation by changing the combination of the LED for illumination and the C-MOS image sensor.

BRIEF DESCRIPTION OF THE DRAWINGS

FIGS. 1 and 2 are diagrams illustrating a first embodiment of the present invention, in which FIG. 1 is a diagram illustrating a construction of an endoscope apparatus having an electronic endoscope of the present invention, and FIG. 2 is a diagram illustrating a construction of the electronic endoscope;

FIGS. 6 and 7 are diagram illustrating a fifth embodiment of the present invention, in which FIG. 6 is a diagrams illustrating a structure of an electronic endoscope of the present invention, and FIG. 7 is a diagram illustrating a specific structure of an electronic endoscope in which an LED backlight is used for an LCD monitor;

FIGS. 10 to 17 are diagrams illustrating a sixth embodiment of the present invention, in which FIG. 10 is a diagram illustrating a structure of an electronic endoscope apparatus having an electronic endoscope of the present invention, FIG. 11 is a diagram illustrating various structural examples of an image pickup adapter, FIG. 12 is a diagram illustrating one structural example of the electronic endoscope, FIG. 13 is a block diagram illustrating one structure of the electronic endoscope, FIG. 14 is a diagram illustrating another structural example of the electronic endoscope;

FIG. 15 is a diagram illustrating still another structural example of the electronic endoscope;

FIG. 16 is a diagram illustrating yet another structural example of the electronic endoscope;

FIG. 17 is a diagram illustrating a structure in a state in which the length of an inserting portion of the electronic endoscope shown in FIG. 12 extends;

FIGS. 18 to 24 are diagrams illustrating a seventh embodiment of the present invention, in which FIG. 18 is a diagram illustrating a structure of an electronic endoscope apparatus having the electronic endoscope of the present invention, FIG. 19 is a diagram illustrating a frame which holds a drum, FIG. 20 is a diagram for illustrating the relationship between an image pickup adapter and the distal end portion of an inserting portion, FIG. 21 is a cross-sectional view for illustrating a structure of the image pickup adapter, FIG. 22 is a diagram for illustrating a C-MOS sensor, a C-MOS sensor power supply circuit substrate, and an LED illustrating power supply circuit substrate, FIG. 23 is a diagram for illustrating an electric system of the endoscope, FIG. 24 is a diagram for illustrating another structural example of the image pickup adapter.

FIG. 29 is a diagram illustrating another structure of the light quantity change-over switch;

DETAILED DESCRIPTION OF THE PREFERRED EMBODIMENTS

Embodiments of the present invention will be described hereinbelow with reference to the drawings.

A first embodiment of the present invention will be described with reference to FIGS. 1 and 2.

Figure 1:
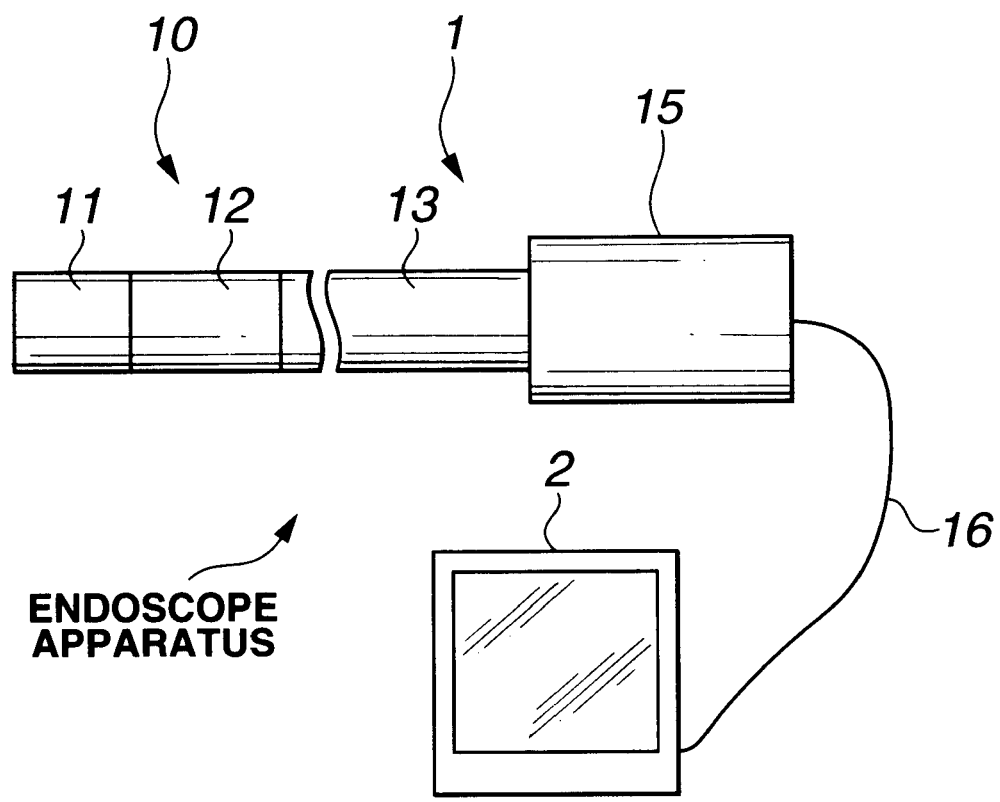

As shown in FIG. 1, an endoscope apparatus according to the present embodiment comprises an electronic endoscope (abbreviated to an endoscope, hereinlater) 1 and a display device 2, e.g., a CRT monitor serving as display means.

The endoscope 1 has, a distal end portion 11 which is made of a hard member, a curved portion 12 which is rotatably formed by arranging a plurality of curved frames in contact with each other, and an inserting portion 10 which is constructed by consecutively providing a flexible tube section 13 which is made of a soft member.

An illuminating section in which an LED for illumination serving as a surface light-emitting light source as illuminating means is disposed, which will be described hereinafter, is arranged at the distal end portion 11. A C-MOS (to which a Complementary Metal-Oxide Semiconductor is abbreviated) image sensor as image pickup means, which will be mentioned hereinafter, is provided at the distal end portion 11. The endoscope 1 is connected to the display device 2 via a video cable 16 which extends from an operating section 15 which also functions as a holding section of the endoscope 1.

Figure 2:
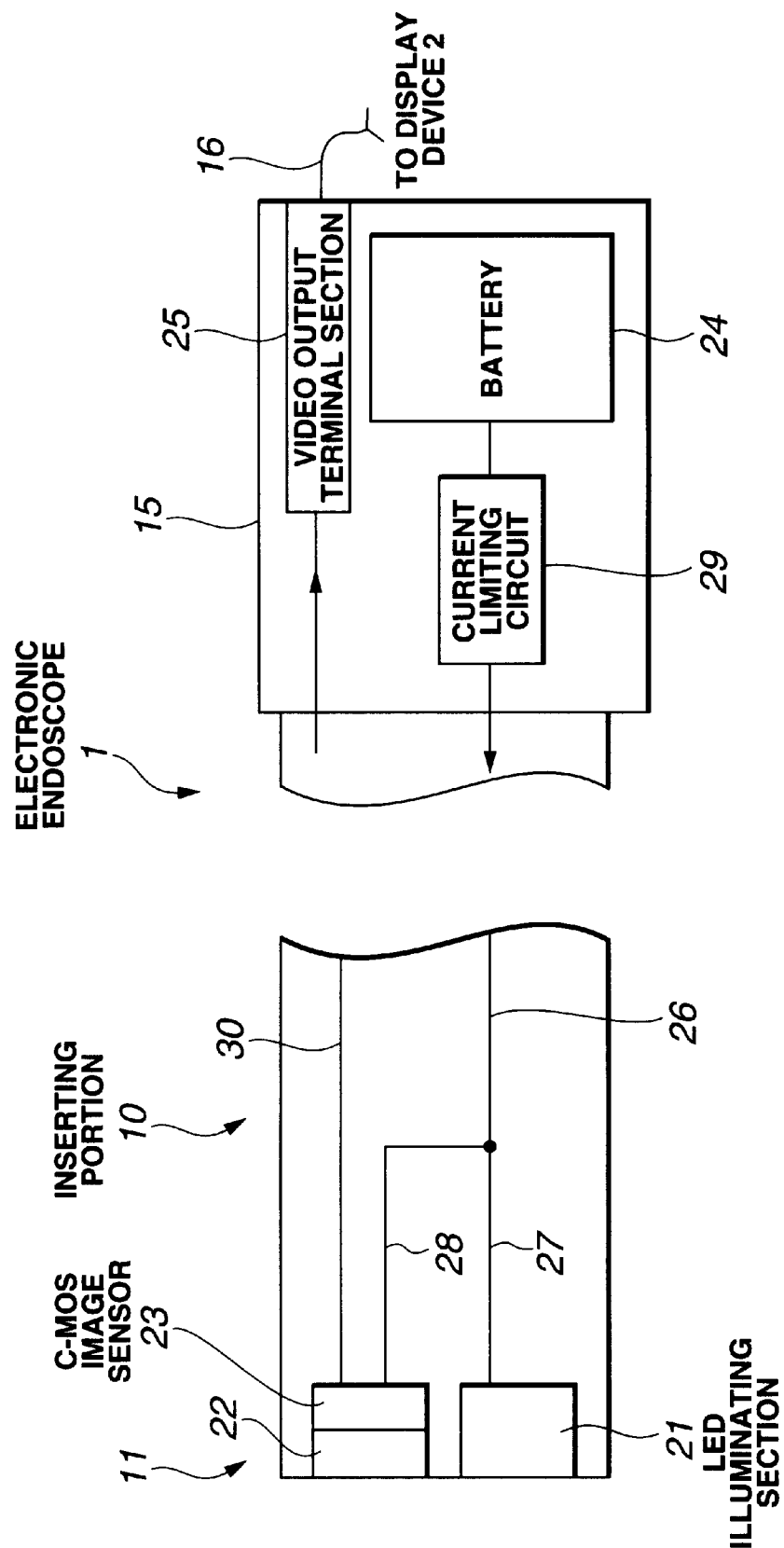

As shown in FIG. 2, the distal end portion 11 of the endoscope 1 is provided therein with an LED illuminating section (abbreviated to an illuminating section, hereinafter) 21 in which, for example, a plurality of LEDs for illumination that illuminate an observed site are disposed, and a C-MOS image sensor (abbreviated to a C-MOS, hereinafter) 23 for photographing an observed image of the observed site that is illuminated by illuminating light which is emitted from the illuminating section 21 through an objective lens 22.

The C-MOS 23 which is used as image pickup means is suitable for the realization of high density in which all functions of a camera, such as a drive signal generating unit, noise cut circuit, output signal level stabilizing circuit, A/D converter are provided and has characteristics in that it is operated by a small power. According to the present embodiment, the C-MOS 23 has characteristics which satisfy the safety standard condition that "the DC is equal to 28 V or less, the amperage is equal to 93 mA or less, and the wattage is 0.66 W or less, as a system including the LED for illumination.

The operating section 15 of the endoscope 1 is provided therein with a battery 24, such as a dry cell or a rechargeable battery, as a power supply section for supplying power to the illuminating section 21 and the C-MOS 23. A video output terminal section 25 serving as a signal output section is provided at, for instance, the basic end portion of the operating section 15. One end of the video cable 16 is connected to the video output terminal section 25.

The battery 24 is electrically connected to the illuminating section 21 and the C-MOS 23 via a cable 26 for power supply which is branched to a cable 27 for illumination and a power supply cable 28 for image pickup device at the intermediate portion.

A current limiting circuit 29 for preventing an excessive current from flowing to the the illuminating section 21 and the C-MOS 23 due to short circuit is provided at the intermediate portion of the cable 26 for power supply.

Further, a video signal transmission cable 30 which extends from the C-MOS 23 and transmits a video signal is electrically connected to the video signal output terminal section 25.

Accordingly, the LED for illumination of the illuminating section 21 which is provided in the endoscope 1 according to the present embodiment is lit by power supplied from the battery 24 provided in the operating section 15, and illuminates the observed site. The observed image of the observed site which is illuminated by the LED for illumination passes through the objective lens 22, is formed on the image pickup surface of the C-MOS 23, is signal-processed into a video signal in the C-MOS 23, and is outputted to the display device 2 via the video output terminal section 25. That is, the observed site can be observed through the endoscope 1 while satisfying the safety standard condition.

The function of the endoscope 1 having the foregoing construction will be described.

First, an operator disposes the display device 2 at a safe region, and brings the endoscope 1 and the video cable 16 in the dangerous place.

Next, the video cable 16 is connected to the video output terminal section 25 and a power supply (not shown) which is provided to the operating section 15 is operated. In other words, a power is supplied to the C-MOS 23 and the illuminating section 21 from the battery 24 which is provided in the operating section 15 via the current limiting circuit 29.

Thus, the illuminating section 21 emits the illuminating light, the observed image which passes through the objective lens 22 is formed on the image pickup surface of the C-MOS 23, a video signal which is outputted from the C-MOS 23 is transmitted to the display device 2 via the video signal transmission cable 30, the video output terminal section 25, and the video cable 16, and the endoscope image of the observed site is displayed on the screen of the display device 2.

An observer performs the observation, etc. while seeing the endoscope image which is displayed on the screen of the display device 2, and also performs desired observation by transmitting an operational instruction to the operator.

As mentioned above, the electronic endoscope is brought in the dangerous place and the observation is performed by the electronic endoscope which is constructed by providing the C-MOS and the LED for illumination which operate under the condition that the DC is equal to 28 V or less, the amperage is equal to 93 mA or less, and the wattage is equal to 0.66 W or less at the distal end portion.

The power supply of the C-MOS and the LED for illumination which is provided at the distal end portion is set as a battery which is provided in the operating section, thereby remarkably improving the mobility.

Further, the current limiting circuit is provided in the operating section, thereby certainly preventing an excessive current from being supplied to the C-MOS and the LED for illumination and enabling the realization of the safety of the electronic endoscope.

A second embodiment of the present invention will be described with reference to FIG. 3.

Figure 3:
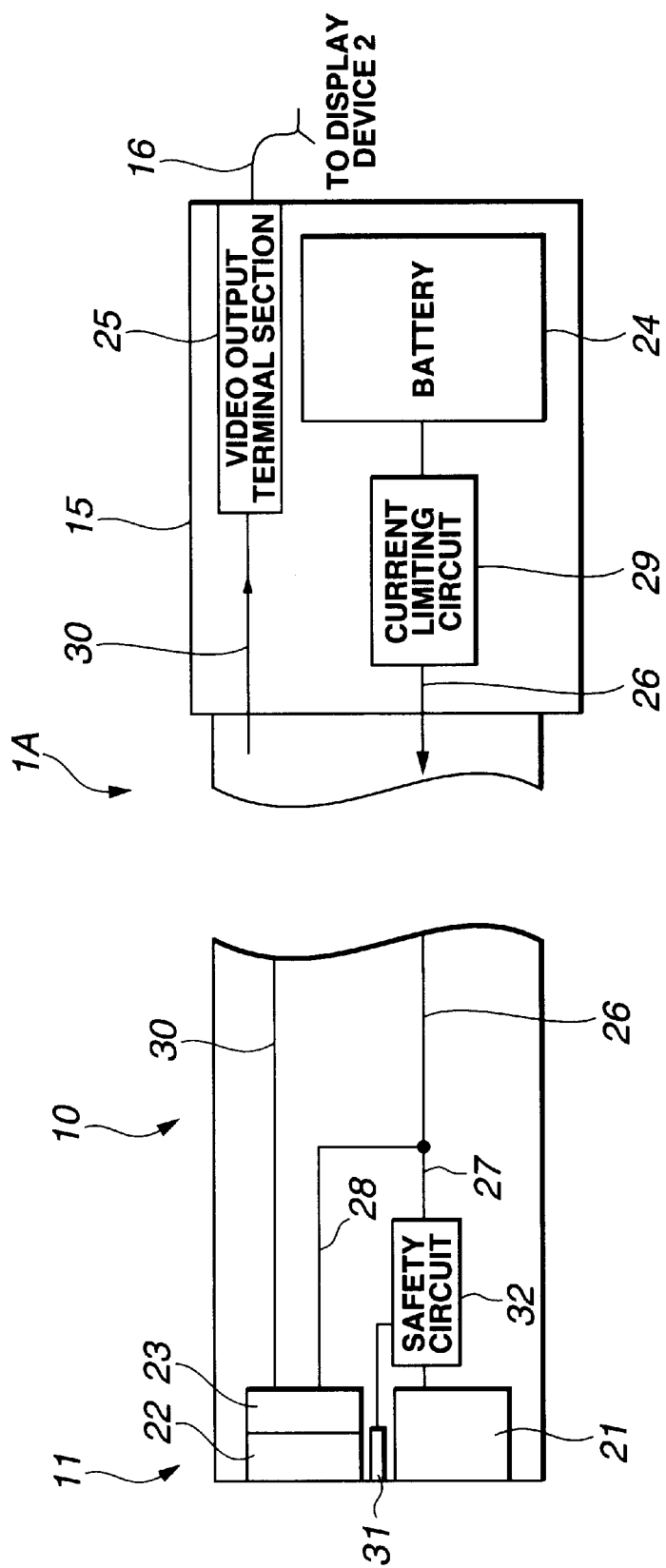
FIG. 3 is a diagram illustrating an electronic endoscope according to a second embodiment of the present invention.

As shown in FIG. 3, a distal end portion 11 of an inserting portion 10 in an electronic endoscope 1A according to the second embodiment is provided with a temperature sensor 31 for detecting the temperature of the distal end portion 11. A safety circuit 32 for control the supply of a power to the illuminating section 21 so as to adjust the quantity of illuminating light in accordance with information of temperature which is transmitted from the temperature sensor 31 is provided at the intermediate portion of the power supply cable 27 for illumination. The other structure is the same as that of the first embodiment, and the same reference symbols are given to the same components and the description is omitted.

As explained above, the temperature near the illuminating section is detected by the temperature sensor, and the temperature at the distal end portion is prevented from increasing up to a predetermined temperature or more due to the heating of the illuminating section by controlling the power to be supplied to the illuminating section by use of the safety circuit. The occurrence of the inconvenience due to the heating can be certainly prevented. The other operations and advantages are the same as those of the first embodiment.

A third embodiment of the present invention will be described with reference to FIG. 4.

Figure 4:
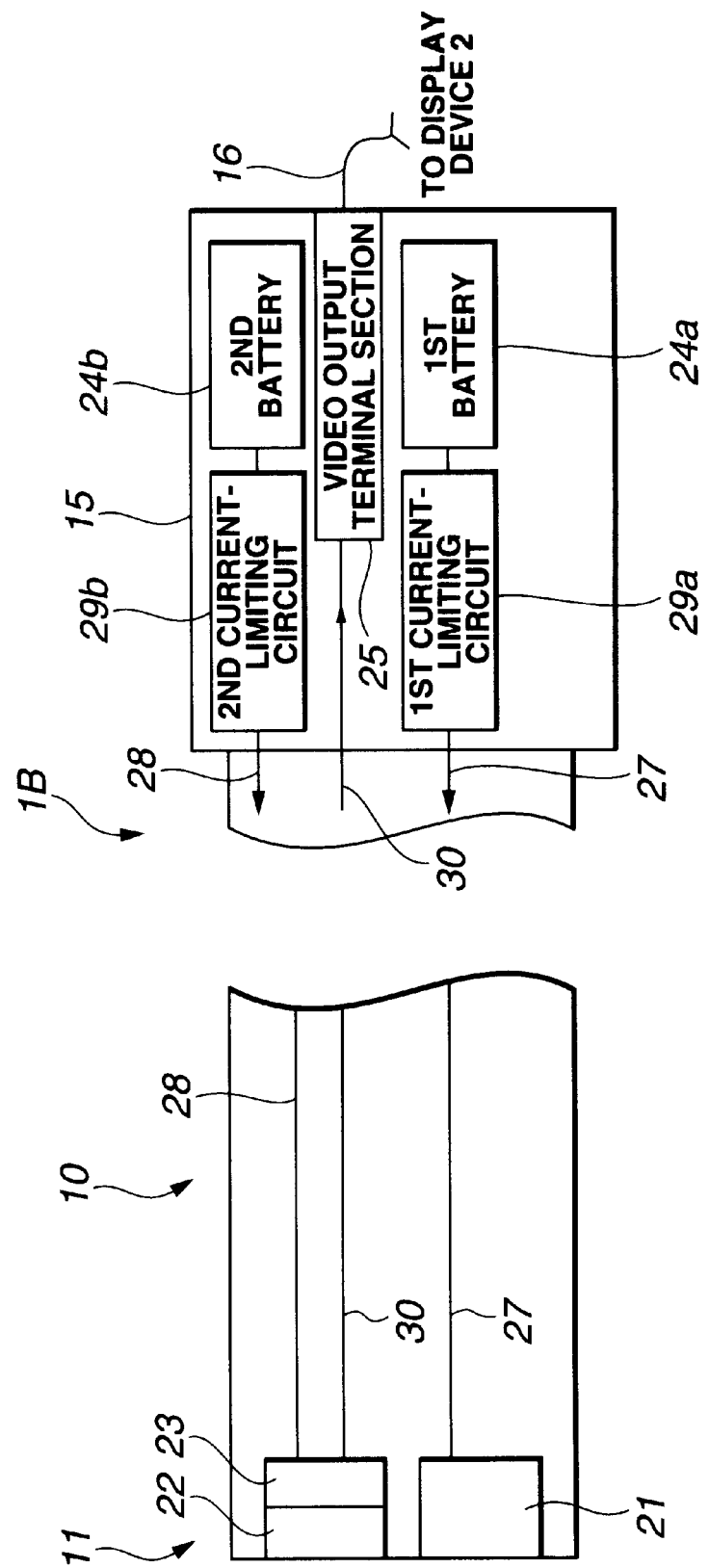
FIG. 4 is a diagram illustrating an electronic endoscope according to a third embodiment of the present invention.

As shown in FIG. 4, according to an electronic endoscope 1B of the third embodiment, a power is supplied to the illuminating section 21 which is provided at a distal end portion 11 thereof by a power supply cable 27 for illumination from a first battery 24a via a first current-limiting circuit 29a. A power is also supplied to the C-MOS 23 by a power supply cable 28 for image pickup device from a second battery 24b via a second current-limiting circuit 29b.

In other words, independent circuits are constructed to the illuminating section 21 and the C-MOS 23, respectively. Thus, a circuit for the illuminating section and a circuit for the C-MOS are independent, respectively, and the safety standard condition "the DC is equal to 28 V or less, the amperage is equal to 93 mA or less, and the wattage is equal to 0.66 W or less," under which the endoscope 1B is available at the dangerous place is satisfied in each circuit. The other structure is the same as that of the first embodiment and the same symbols are given to the same components and the description is omitted.

As explained above, the circuit for the illuminating section and the circuit for the C-MOS are independent, respectively, and the safety standard condition "the DC is equal to 28 V or less, the amperage is equal to 93 mA or less, and the wattage is equal to 0.66 W or less," under which the endoscope 1B is available at the dangerous place is satisfied in each circuit. Thereby, it is possible to sufficiently supply a power to the illuminating section and to obtain a sufficient quantity of illuminating light. The other operations and advantages are the same as those of the first embodiment.

A fourth embodiment of the present invention will be described with reference to FIG. 5.

Figure 5:
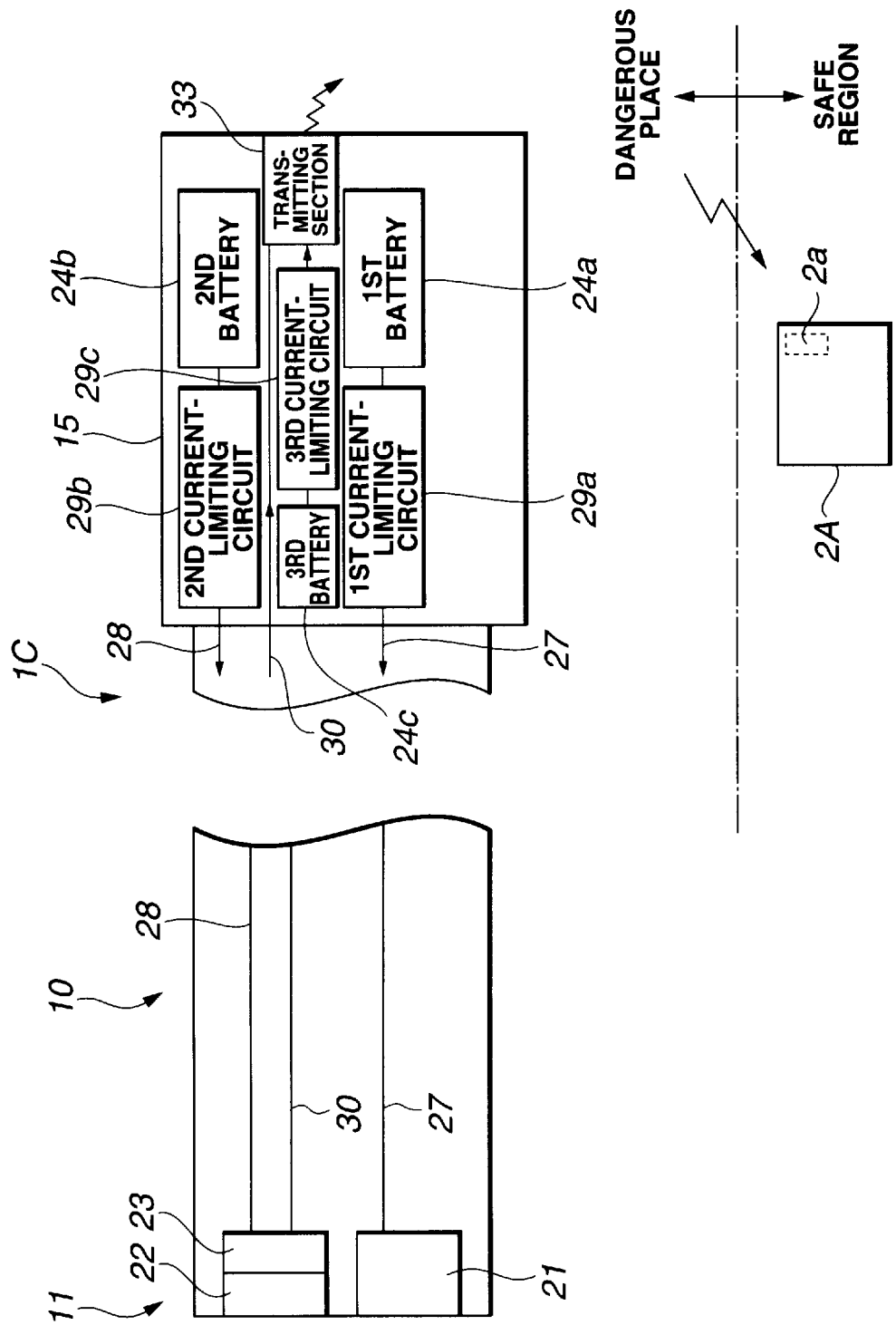
FIG. 5 is a diagram illustrating a structure of an electronic endoscope according to a fourth embodiment of the present invention.

As shown in FIG. 5, according to an electronic endoscope 1C of the four embodiment, in place of providing the video output terminal section 25 as the signal output section in an operating section 15, a transmitting section 33 for outputting a weak radio wave or infrared light which is available at dangerous places is provided therein. A power is supplied to the transmitting section 33 by a third battery 24c. A third current-limiting circuit 29c is provided between the third battery 24c and the transmitting section 33. In place of the display device 2, at least one display device 2A having a receiving section 2a and a recording device (not shown) are used.

Incidentally, the first battery 24a or the second battery 24b may become a power supply section of the transmitting section 33. In this case, a current limiting circuit is provided between the transmitting section 33 and the batteries 24a and 24b. The other structure is the same as that of the second embodiment and the same reference symbols are given to the same components and the description is omitted.

As explained above, it is possible to execute the observation and the recording by transmitting a signal to the receiving section of the display device, etc. which is disposed at the safety region from the transmitting section which is provided in the operating section. Thus, a video cable, etc. via which the dangerous place is connected to the safety region are unnecessary and the mobility, operability, and free degree of operation of the endoscope are largely improved. The other operations and advantages are the same as those of the first embodiment.

Although, according to the present embodiment, the objective lens and the illuminating section are provided at the surface of the distal end, the objective lens and the illuminating section may be provided at the side portion, etc.

If the display device 2 is observed in the dangerous place, a display device which satisfies the safety standard condition is used.

Further, although, according to the above-mentioned embodiments, the electronic endoscope is described as the electronic endoscope which is used in the dangerous places, the structure of the present embodiment may be applied to an industrial endoscope and a medical endoscope which are used in the safe region.

Although, according to the present embodiment, the power supply section is the battery, the power supply section is not limited to a battery and may be an external power supply having a power supply limiting circuit. When the power supply is an external power supply, it is possible to further simplify the structure of the operating section by controlling a current value on the side of the external power supply.

A fifth embodiment of the present embodiment will be described with reference to FIG. 6 and FIG. 7.

According to an electronic endoscope of the fifth embodiment, an operator which operates the endoscope at the dangerous place can observe an endoscope image.

As shown in FIG. 6, according to an electronic endoscope 1D of the fifth embodiment, an LCD monitor 40 is provided as a display section at the basic end portion of an operating section 15 which also functions as a holding section that is provided at the basic end of an inserting portion 10.

Specifically speaking, the LCD monitor 40 is the LCD monitor with an LED backlight (abbreviated to the monitor a with the backlight, hereinafter) 40 in which an LED backlight 41 is arranged as a backlight, as shown in FIG. 7, and operates while satisfying "the DC is equal to 28 V or less, the amperage is equal to 93 mA or less, and the wattage is equal to 0.66 W or less".

As shown in FIG. 6 and FIG. 7, a battery 24 such as a dry cell is arranged as a power supply section for supplying a power to the illuminating section 21, the C-MOS 23, and the monitor 40 with backlight in the operating section 15 of the endoscope 1D.

A video signal transmission cable 30 which extends from the C-MOS 23 and transmits a video signal is electrically connected to the monitor 40 with the backlight. The monitor 40 with the backlight is driven by a power which is supplied from the battery 24 via the current limiting circuit 29.

Thus, according to the endoscope 1D, an observed site as a target can be observed at the dangerous places while satisfying the safety standard condition "the DC is equal to 28 V or less, the amperage is equal to 93 mA or less, and the wattage is equal to 0.66 W or less".

The operation of the endoscope 1D will be described.

First, a user brings the endoscope 1D in the dangerous place and operates a power supply switch (not shown) which is provided in the operating section 15. Then, a power is supplied to the illuminating section 21, the C-MOS 23, and the monitor 40 with backlight from the battery 24 which is provided in the operating section 15 via the current limiting circuit 29.

Thus, the LED for illumination in the illuminating section 21 is lit on and illuminating light is emitted to an observed site. An observed image of the observed site passes through the objective lens 22, is formed on an image pickup surface of the C-MOS 23, and signal-processed into a video signal in the C-MOS 23. The video signal which is signal-processed in the C-MOS 23 passes through the video signal transmission cable 30, is transmitted to the monitor 40 with backlight, and an endoscope image of the observed site is displayed on a screen of the display section. Therefore, an observer can operate the endoscope 1D while observing the endoscope image which is displayed on the screen of the monitor 40 with backlight.

As mentioned above, the electronic endoscope is constructed by providing the C-MOS and the LED for illumination at the distal end portion, providing the monitor with backlight in the operating section, and providing the battery serving as a power supply of the C-MOS, the LED for illumination, and the monitor with backlight in the operating section and the electronic endoscope operates as a system under the condition that the DC is equal to 28 V or less, the amperage is equal to 93 mA or less, and the wattage is equal to 0.66 W or less. Accordingly, it is possible to provide an electronic endoscope which has excellent mobility and, observability and safety for use in dangerous places.

By providing the current limiting circuit, it is possible to certainly prevent an excessive current from flowing to the C-MOS, the LED for illumination, and the monitor with backlight and to safely use the electronic endoscope.

One structural example which is obtained by applying the fifth embodiment will be described with reference to FIG. 8.

Figure 8:
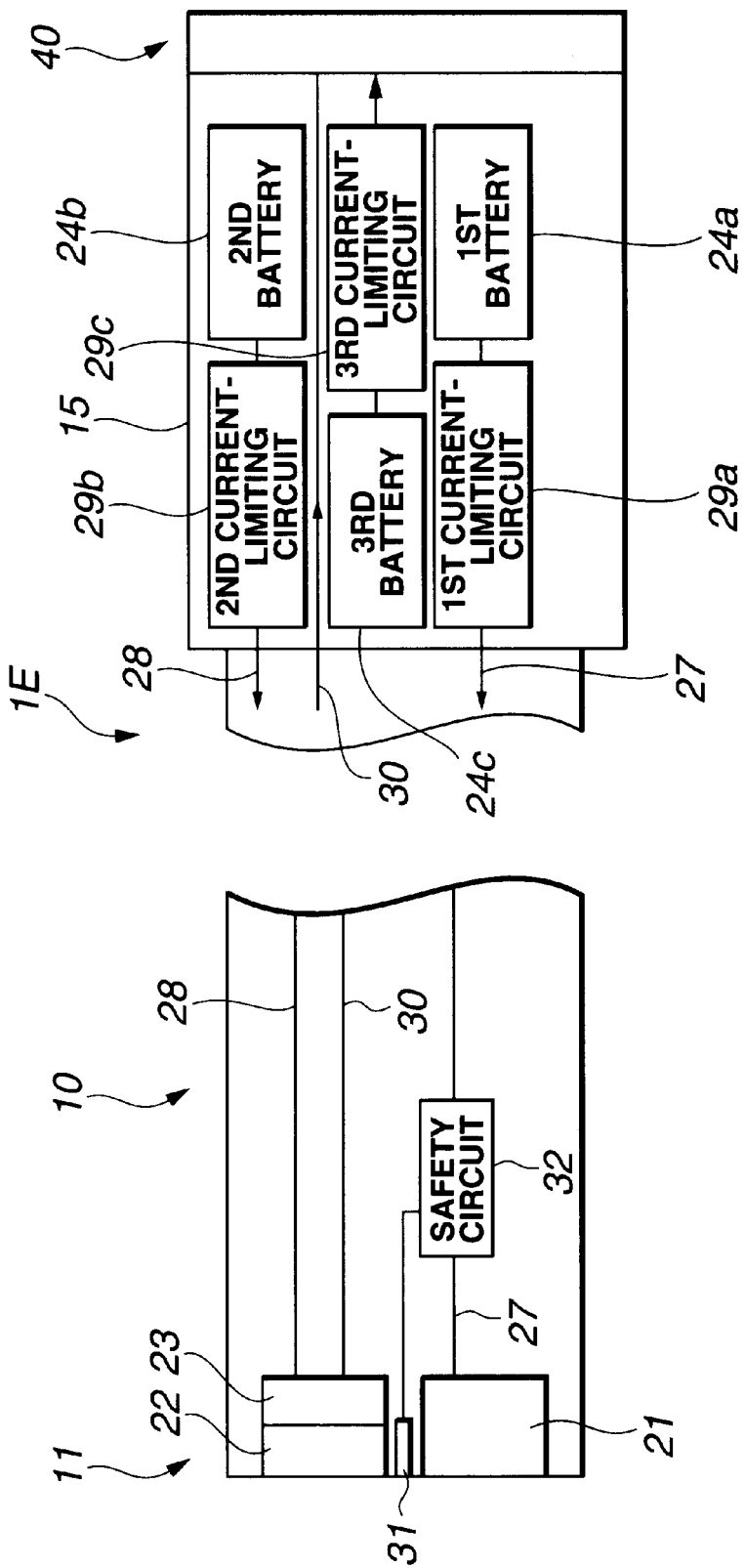
FIG. 8 is a diagram illustrating one application of the electronic endoscope according to the fifth embodiment.

As shown in FIG. 8, an electronic endoscope 1E according to the present embodiment has a circuit which supplies a power to the illuminating section 21 by a power supply cable 27 from a first battery 24a via a first current-limiting circuit 29a, a circuit which supplies a power to the C-MOS 23 by a power supply cable 28 for image pickup device from a second battery 24b via a second current-limiting circuit 29b and, further, a circuit which supplies a power to the monitor 40 with backlight from a third battery 24c via a third current-limiting circuit 29c, which are independent.

Thereby, the circuits supplies a power to the illuminating section 21, the C-MOS 23, and the monitor 40 with backlight while satisfying the safety standard condition under which the circuits are available in the dangerous places. Thus, by supplying a power which can sufficiently derive the characteristics of the illuminating section 21, the C-MOS 23, and the monitor 40 with backlight such as the increase in the number of the LEDs for illumination which constructs the illuminating section and, thereby, the increase in the quantity of illuminating light, a preferable observation can be performed. Incidentally, in the present figure, the endoscope 1E has therein the temperature sensor 31 and the safety circuit 32.

Another structural example which is obtained by applying the fifth embodiment will be described with reference to FIG. 9.

Figure 9:
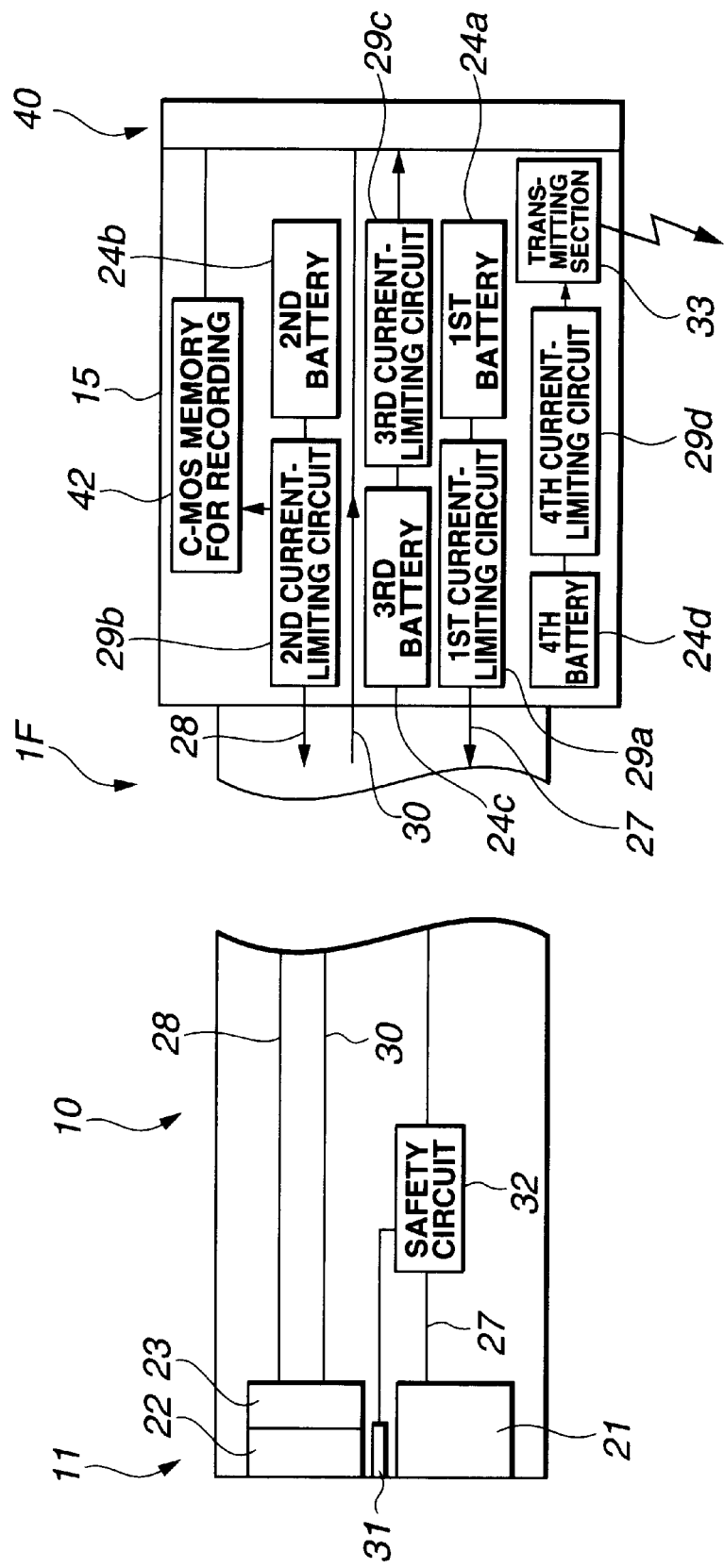
FIG. 9 is a diagram illustrating another application of the electronic endoscope according to the fifth embodiment.

As shown in FIG. 9, an electronic endoscope 1F has therein, for example, a transmitting section 33 serving as a signal output section for transmitting a video signal to an operating section 15, and a C-MOS memory 42 for recording in which an image, etc. during the observation are stored.

By providing the transmitting section 33, a weak radio wave and infrared light which are available in the dangerous places are outputted to the display device (refer to reference numeral 2A in FIG. 5) having the receiving section that is arranged in the safe region and the same endoscope image as the endoscope image which is displayed on the monitor 40 with backlight is displayed on the display device. Thus, not only the user but also a plurality of participants can simultaneously observe the observed site.

Then, in this case, for instance, a fourth battery 24d as another battery supplies a power to the transmitting section 33 and a fourth current-limiting circuit 29d is provided between the fourth battery 24d and the transmitting section 33. A power is supplied to the C-MOS memory 42 for recording via the current limiting circuit by the common use of any one of the batteries 24a, 24b, 24c, and 24d or by providing another battery. According to the present embodiment, the second battery 24b is commonly used and a power is supplied to the C-MOS memory 42 for recording via the second current-limiting circuit 29b.

A sixth embodiment of the present invention will be described with reference to FIGS. 10 to 17.

According to an electronic endoscope of the present embodiment, an image pickup adapter having a C-MOS image sensor and an LED for illumination as an illuminating section is detachable to the distal end portion of an inserting portion of the endoscope. Incidentally, the electronic endoscope according to the present embodiment is described as an industrial endoscope.

Figure 10:
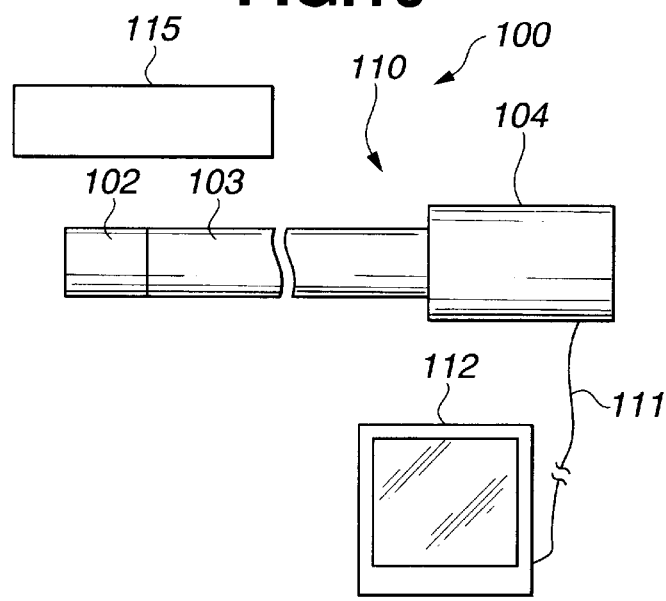

As shown in FIG. 10, an endoscope apparatus 100 according to the present embodiment has an endoscope 110 in which a plurality of kinds of image pickup adapters 102 having therein an LED for illumination and a C-MOS image sensor that have varied structures in correspondence to an inspecting situation and an inspecting purpose can be detachably arranged at the distal end portion of an inserting portion 103. An endoscope image which is captured through the endoscope 110 is displayed on a display device 112 such as a CRT monitor which is connected to a video cable 111 that extends from an operating section 104. Then, the image pickup adapter 102 is detachably connected and fixed by fixing means, e.g., a screw (not shown). Reference numeral 115 denotes an inserting portion extending member which is used when the length of the inserting portion, which will be mentioned later on, extends.

Figure 11A:
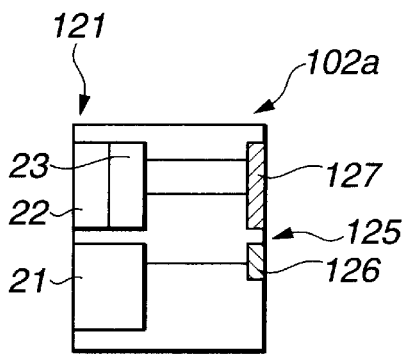
FIG. 11A is a diagram showing one structural example of the image pickup adapter.
Figure 11B:
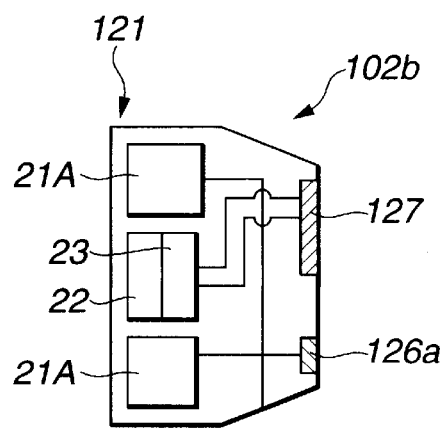
FIG. 11B is a diagram showing another structure of the image pickup adapter.
Figure 11C:
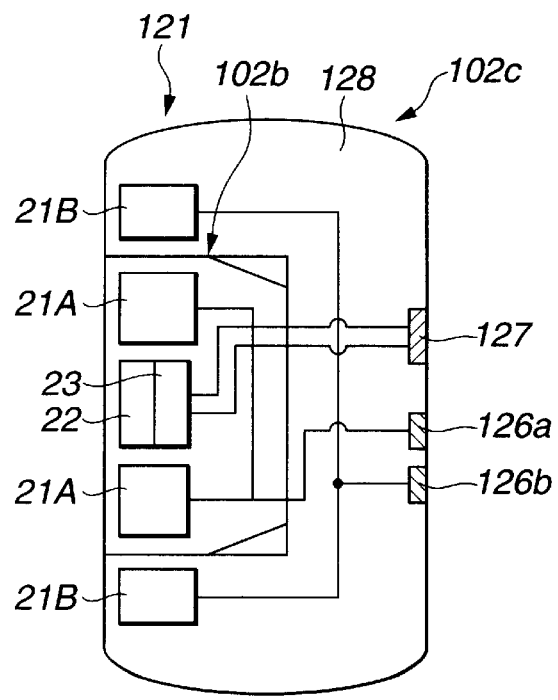
FIG. 11C is a diagram showing still another structure of the image pickup adapter.

Types of the image pickup adapter shown in FIGS. 11A, 11B, and 11C are exemplified as the image pickup adapters 102.

An image pickup adapter 102a shown in FIG. 11A has therein an illuminating section 21 in which a plurality of LEDs for illumination that illuminate an observed site to a distal side 121 of the adapter and a C-MOS 23 for photographing an observed image of the observed site which is illuminated by illuminating light that is emitted from the illuminating section 21. An LED connecting section 126 on the adapter side and a C-MOS connecting section 127 on the adapter side are provided as electric connecting sections on, for instance, a basic-end surface 125 serving as an outer surface of the image pickup adapter 102. Then, an objective lens 22 for forming the observed image on the image pickup surface is arranged on the front side of the C-MOS 23.

According to an image pickup adapter 102b shown in FIG. 11B, illuminating sections 21A are arranged while sandwiching a C-MOS 23, and the quantity of illuminating light is larger as compared with that of the image pickup adapter 102a. By providing the illuminating sections 21A while sandwiching the C-MOS 23, the external dimension is larger than that of the image pickup adapter 102a.

An image pickup adapter 102c shown in FIG. 11C is a centering device 128 in which the image pickup adapter 102b is integrally arranged and has therein an illuminating section 122B for multiple flashes. The structure results in further increasing the quantity of illuminating light.

Set positions of the C-MOS connecting sections 127 on the adapter side which are set to the image pickup adapters 102a, 102b, 102c, . . . exist at the same position in views of positions from the central position of all of the image pickup adapters 102a, 102b, 102c, . . . . On the other hand, set positions of LED connecting sections 126, 126a, 126b, . . . , 126n on the adapter side are determined for the illuminating sections 21, 21A, 21B, . . . , 21N, respectively.

Although another structure of the image pickup adapter 102 is not shown, there are image pickup adapters corresponding to various applications such as ones having C-MOSs of a different number of pixels and ones having C-MOSs of different pixel construction. In the image pickup adapter 102c, the centering device 128 is detachable to the inserting portion 103.

The structure of the electronic endoscope 110 will be specifically described with reference to FIGS. 12 and 13.

Figure 12:
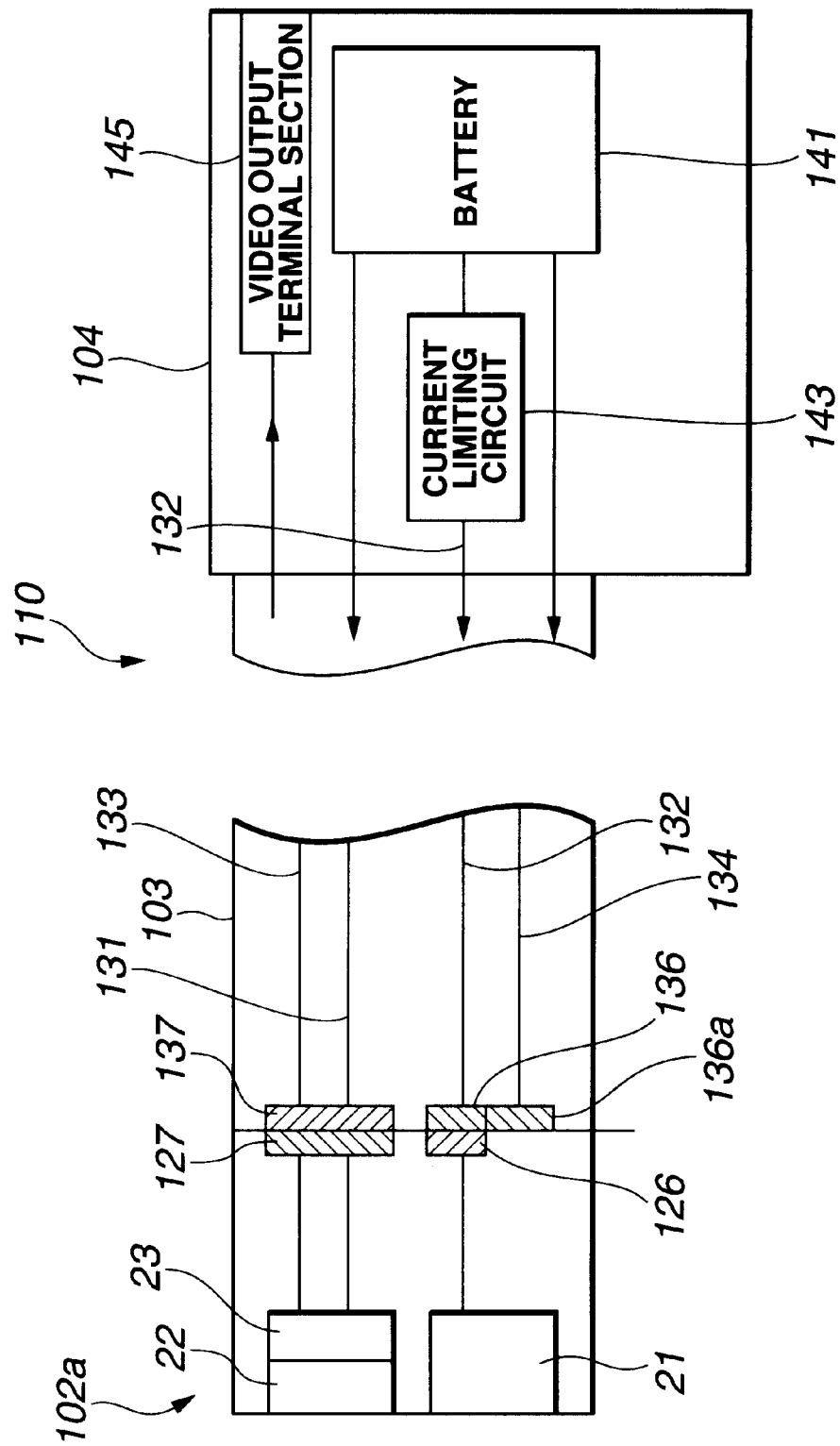
Figure 13:
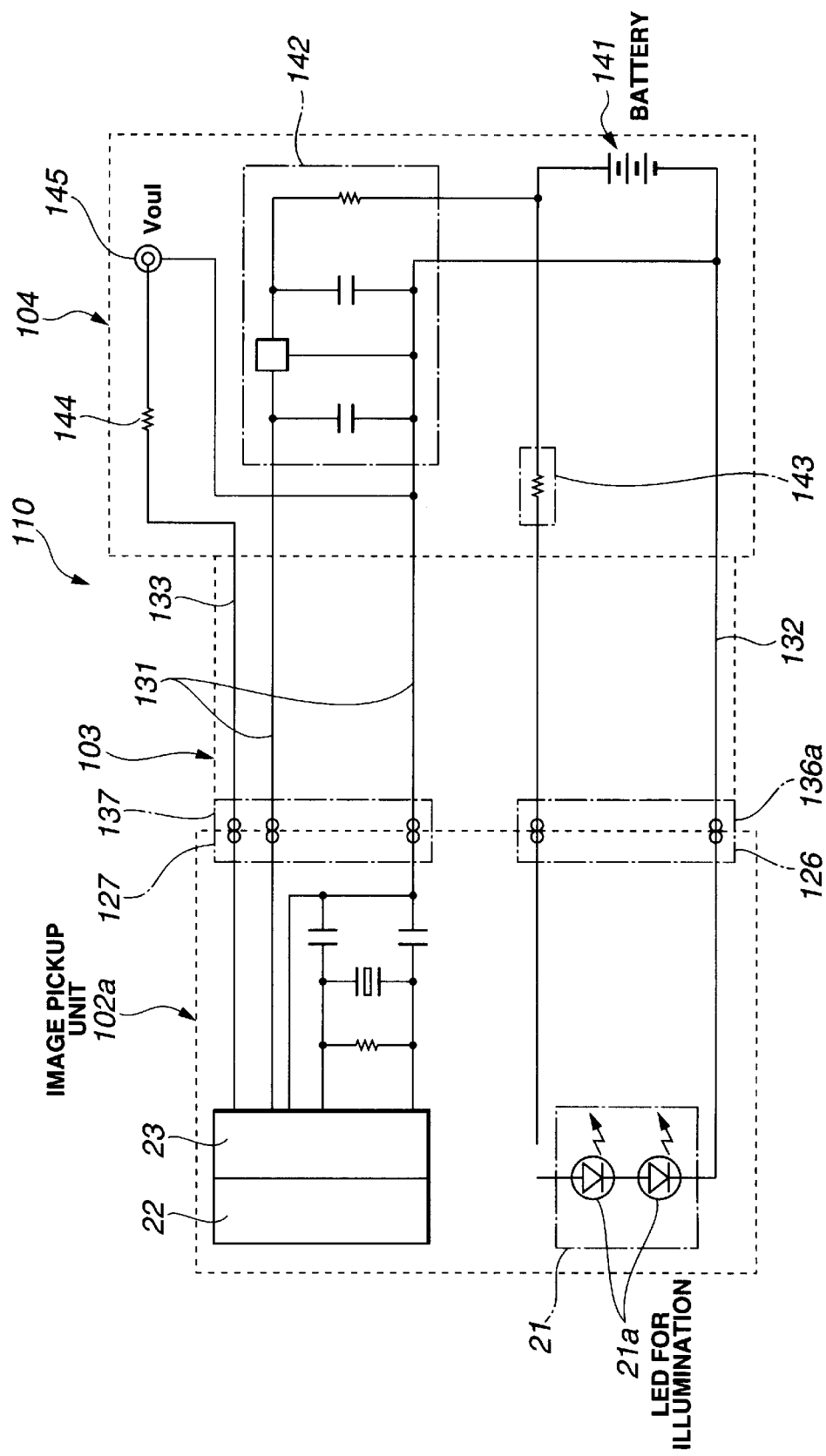

As shown in FIGS. 12 and 13, according to the electronic endoscope 110, for example, an image pickup adapter 102a is connected and fixed to the surface of a distal end portion of an inserting portion 103.

An LED connecting section 136 on an inserting portion side and a C-MOS connecting section 137 on the inserting portion side which are electrically connected to an LED connecting section 126 of the adapter and a C-MOS connecting section 127 on the adapter side that are provided on the surface of a basic end of the image pickup adapter 102a are provided on the basic-end surface 125 of the distal end portion of the inserting portion 103.

A driving cable 131 as an electric cable for electrically connecting the C-MOS connecting section 137 on the inserting portion side to a battery 141 as a power supply section which is provided in an operating section 104 and for supplying a drive power to the C-MOS 23, a cable 132 for illumination as an electric cable for electrically connecting the LED connecting section 136 on the inserting portion side to the battery 141 and for supplying a power for illumination to one or plurality of LEDs 21a for illumination which construct the illuminating section 21, and a signal transmission cable 133 as an electric cable which extends from the C-MOS connecting section 137 on the inserting portion and transmits a video signal that is generated by the C-MOS 23 to a video output terminal section 145, which will be described later on, are inserted in the inserting portion 103.

A constant voltage circuit 142, which stabilizes power supplied to the C-MOS 23, and a current limiting circuit 143, which is located at the intermediate portion of the cable 132 for illumination to connect the battery 141 to the illuminating section 21 and limits a value of a current that is supplied to the illuminating section 21 to a predetermined value, are provided in the operating section 104.

The video output terminal section 145 to which a video cable 111 for transmitting the video signal that is outputted by the C-MOS 23 to a display device 112 is detachably connected is provided at, e.g., the end portion of the operating section 104. The signal transmission cable 133 is electrically connected to the video output terminal section 145 via a resistor 144.

Incidentally, reference numeral 136a denotes an LED connecting section on the inserting portion side which is electrically connected to the LED connecting section 126a on the adapter side that is provided to the image pickup adapter 102b. Reference numeral 134 denotes a cable for illumination which electrically connects the LED connecting section 136a on the inserting portion side to the battery 141 and supplies a power for illumination to the LED for illumination that constructs an illuminating section 21A in the image pickup adapter 102b.

Figure 14:
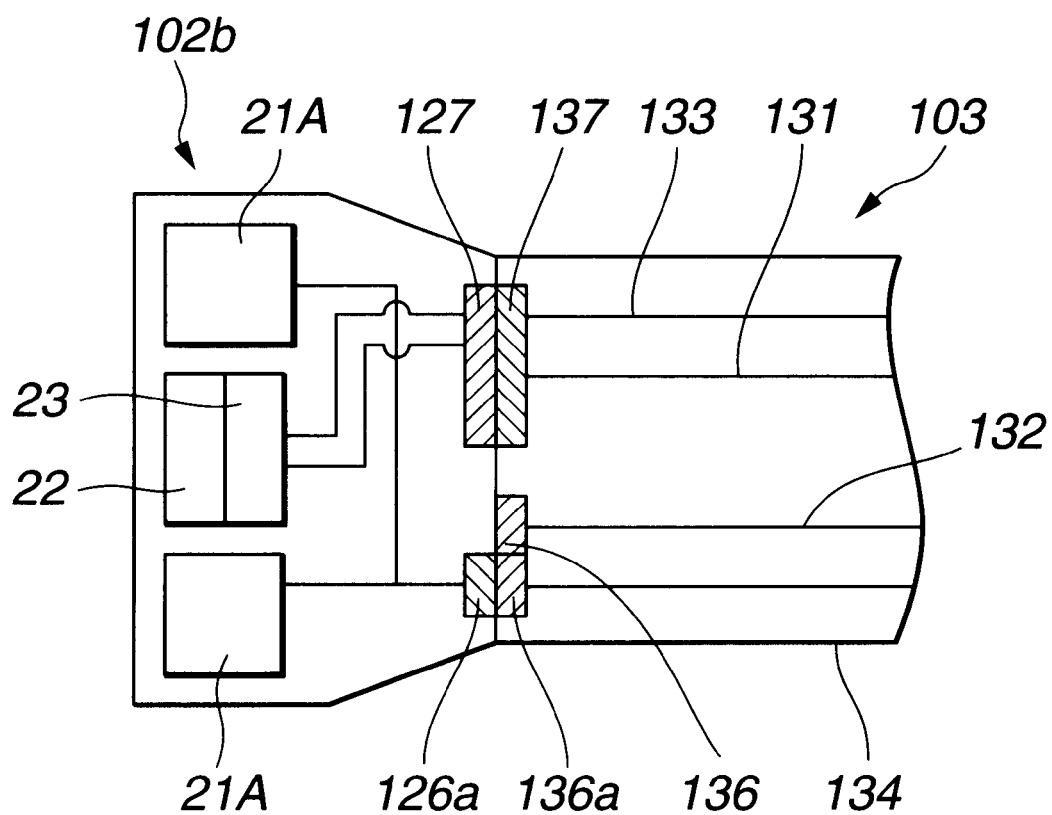

When the image pickup adapter 102b is connected and fixed to the surface of the distal end portion of the inserting portion 103 with the construction as shown in FIG. 14, the power for illumination is supplied an LED for illumination (not shown) in the illuminating section 21A that is provided in the image pickup adapter 102b via the cable 134 for illumination, the LED connecting section 136a on the inserting portion side, and the LED connecting section 126a on the adapter side from the battery 141, not passing through the current limiting circuit 143.

That is, the battery 141 shown in the present figure is set so as to supply a current having a proper value to the illuminating section 21A that is provided in the image pickup adapter 102b. Therefore, if the image pickup adapter 102a is provided at the surface of the distal end portion of the inserting portion 103, the value of current needs to be limited and, thus, a power for illumination is supplied to the illuminating section 21 via the current limiting circuit 143.

In other words, by changing a supply circuit every image pickup adapter, an excessive current is prevented from flowing to the illuminating section 21 when the image pickup adapter 102a is mounted.

Figure 15:
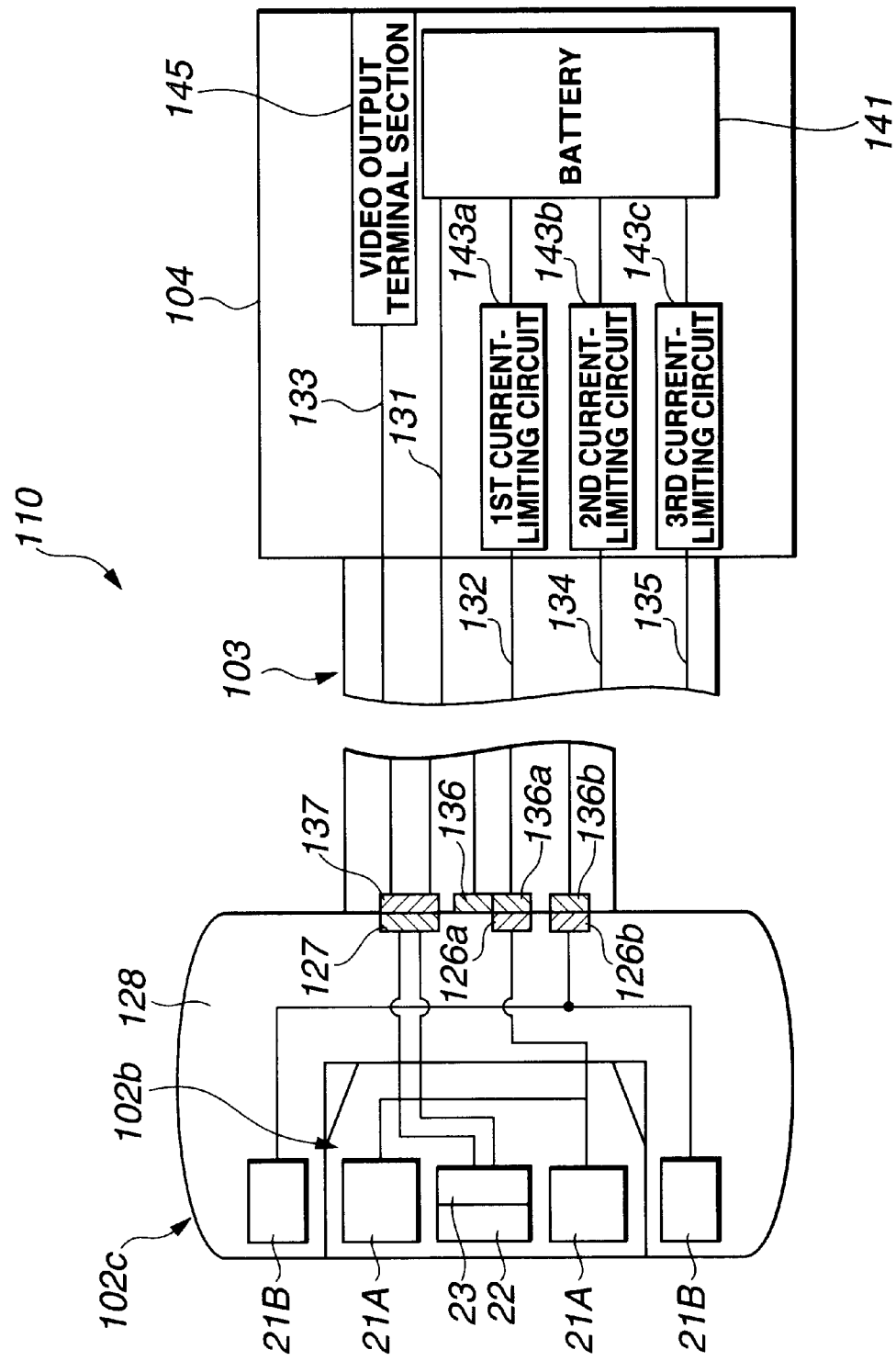

In order to enable the image pickup adapter 102c to be connected to the inserting portion 103, an LED connecting section 136b on the inserting portion side which is electrically connected to an LED connecting section 126b on the adapter side that is further provided in the centering device 128 is provided at the surface of the distal end portion of the inserting portion 103, as shown in FIG. 15. This results in supplying a power for illumination to an illuminating section 21A and an illuminating section 21B of the image pickup adapter 102c and brightly illuminating a wide range.

In this case, a first current-limiting circuit 143a, a second current-limiting circuit 143b, and a third current-limiting circuit 143c are provided to the cables 132, 134, and 135 for illumination which are inserted in the inserting portion 104, respectively, and thus an excessive current is prevented from flowing to the illuminating sections 21A and 21B and the illuminating section 21.

Figure 16:
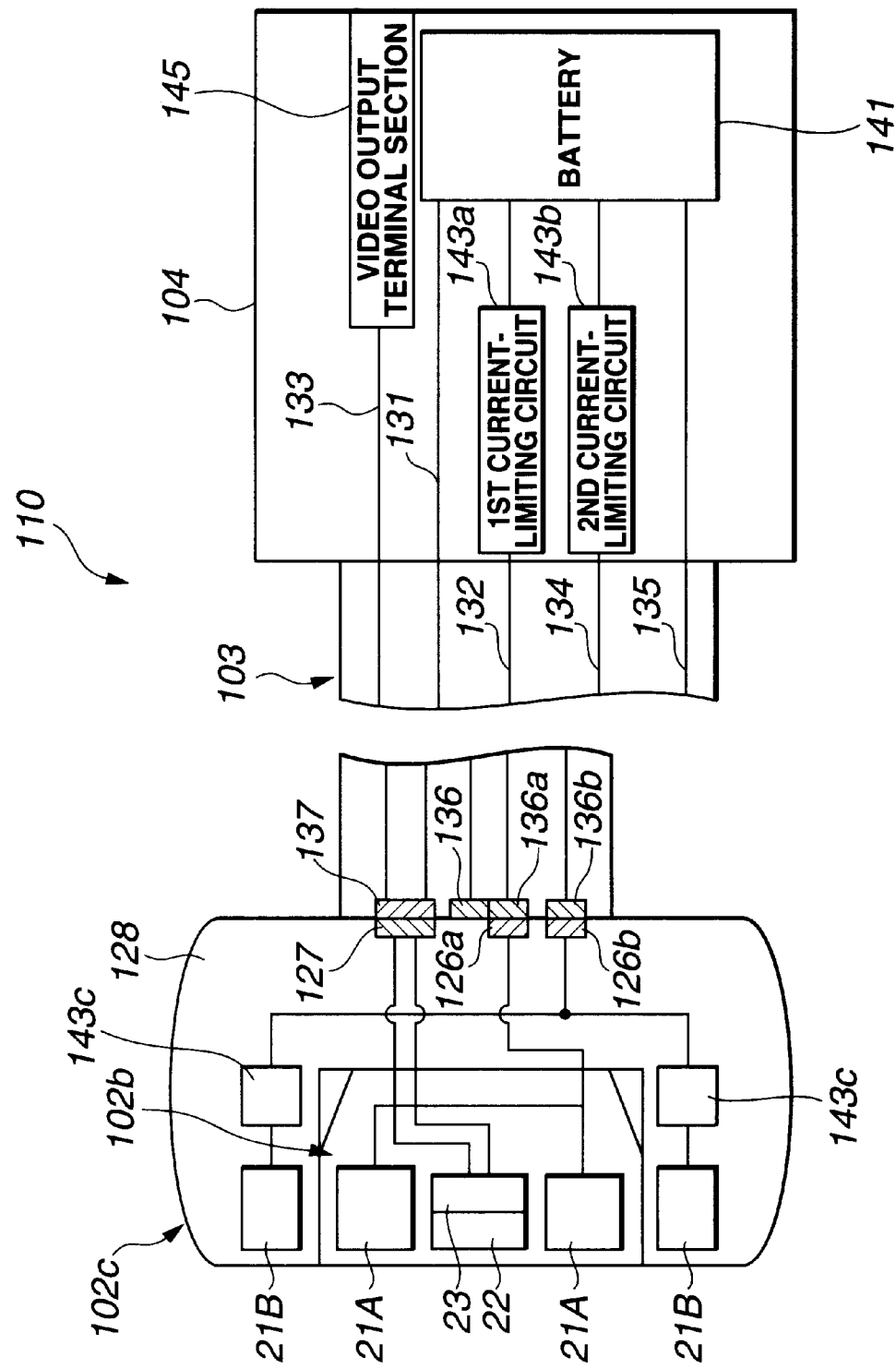

If heating of the LED for illumination gives no harmful influence and the centering device 128 confirms that heat is sufficiently dissipated, the current limiting circuit 143c may be provided to a space on the side of the centering device 128 in order to simplify the operating section 104 as shown in FIG. 16.

The operation of the endoscope 110 with the foregoing structure will be described.

First, the user selects the image pickup adapter 102 which builds in the C-MOS 23 having a desired number of pixels and a pixel construction and the illuminating section 21 according to the diameter and the inspecting purpose of a piping as an observed target and mounts the image pickup adapter 102 in the inserting portion 103. The video cable 111 is connected to the display device 112 and the video output terminal section 145.

Next, the user operates a switch (not shown) which is provided in the operating section 104 and, thus, a power is supplied to the C-MOS 23 and the illuminating section 21. Then, a video output signal which is subjected to an image process by the C-MOS 23 and outputted is transmitted to the display device 112 and an endoscope image of the observed site which is illuminated by the illuminating section 21 is displayed on the screen.

Figure 17:
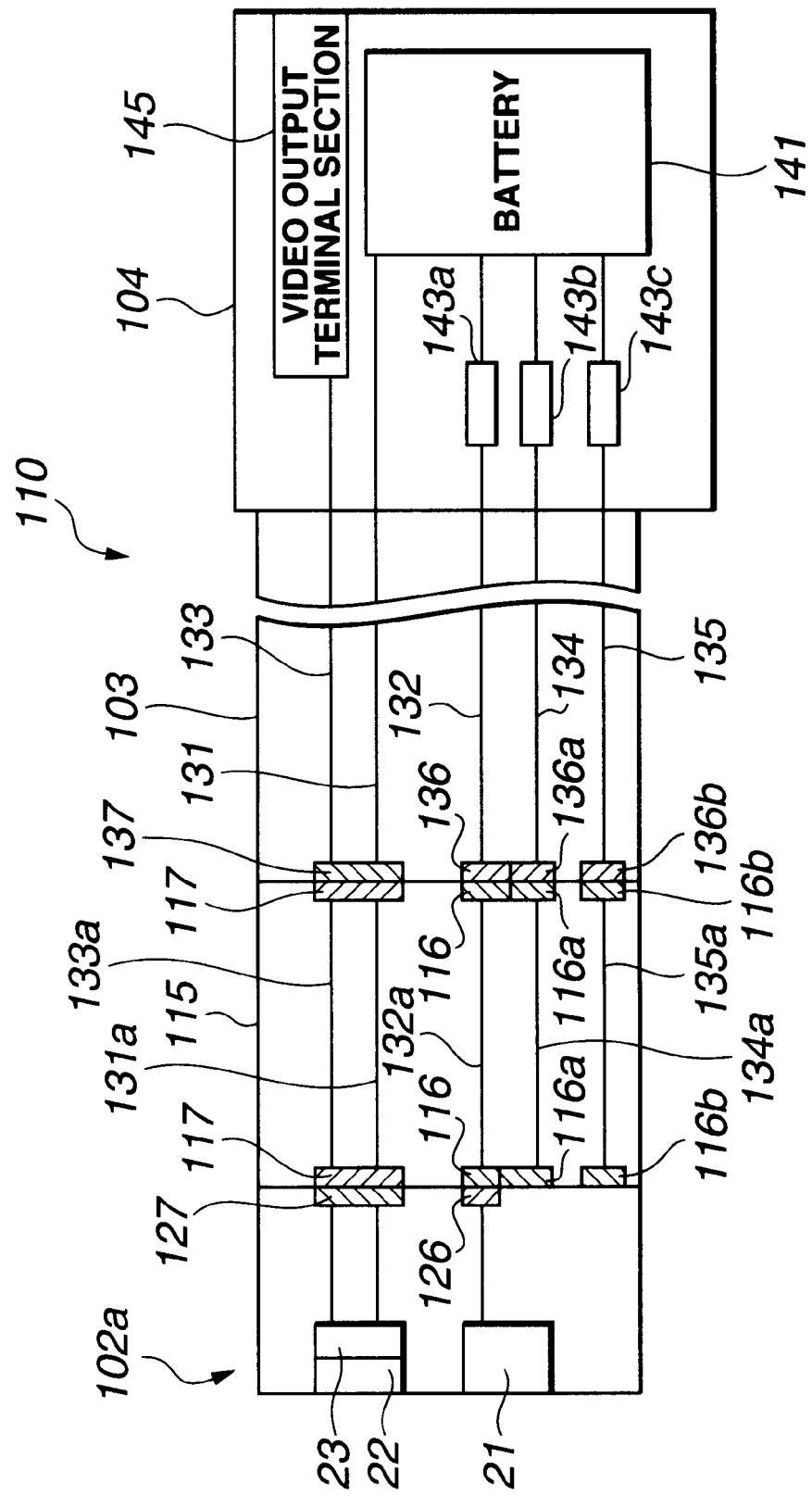

Herein, if a desired image is not obtained when the endoscope image is observed, the user properly exchanges the image pickup adapter 102 and observes the observed site. For example, if the image pickup adapter 102a does not reach the observed site as a target because the length of the inserting portion of the electronic endoscope 110 is short, the inserting portion extending member 115 is mounted as shown in FIG. 17 and the user observes the observed site.

As shown in the figure, a C-MOS connecting section 117 for extension as an electric connecting section which is electrically connected to the C-MOS connecting section 127 on the adapter side and LED connecting sections 116, 116a, and 116b for extension as electric connecting sections which are electrically connected to the LED connecting sections 126, 126a, and 126b on the adapter side are provided at the end portion on the side of the distal end portion of the inserting portion extending member 115. The C-MOS connecting section 117 for extension as an electric connecting section which is electrically connected to the C-MOS connecting section 137 on the inserting portion side and the LED connecting sections 116, 116a, and 116b for extension as electric connecting sections which are electrically connected to the LED connecting sections 136, 136a, and 136b on the inserting portion side are provided at the end portion on the side of the basic portion. The connecting sections are electrically connected via a driving cable 131a, cables 132a, 134a, and 135a for illumination, and a transmission signal cable 133a which correspond thereto, respectively.

That is, when the inserting portion extending member 115 is connected and fixed between the image pickup adapter 102a and the inserting portion 103, the C-MOS connecting section 117 for extension on the side of one end of the inserting portion extending member 115 and the LED connecting sections 116, 116a, and 116b for extension are electrically connected to the C-MOS connecting section 127 on the adapter side of the image pickup adapter 102a and the LED connecting sections 126, 126a, and 126b on the adapter side, respectively. The C-MOS connecting section 117 for extension on the side of the other end and the LED connecting sections 116, 116a, and 116b for extension are electrically connected to the C-MOS connecting section 137 on the inserting portion side and the LED connecting sections 136, 136a, and 136b on the inserting portion side, respectively.

Thus, the electronic endoscope 110 is structured in a manner that a power can be supplied to the C-MOS 23 and the illuminating sections 21, 21A, and 21B and the video signal which is outputted by the C-MOS 23 can be transmitted to the video output terminal section 145, and the length of the inserting portion corresponding to the length of the inserting portion extending member 115 is extended.

Incidentally, a plurality of inserting portion extending members such as the inserting portion extending members 115a, 115b, . . . which have different lengths may be prepared. By providing a detached portion for mounting the inserting portion extending member 115 nearer the side of the operating section as much as possible, it is possible to change the length of the inserting portion during the working.

As mentioned above, the electronic endoscope is constructed by detachably providing the image pickup adapter in which the image pickup device for outputting the video output and the light source section corresponding to the characteristics of the image pickup device at the distal end portion of the inserting portion and, thereby, the endoscope image with a preferable image quality can always be displayed on the screen of the display device, irrespective of not only the change in the number of pixels and the pixel construction but also the change in length of the inserting portion.

The user freely sets the length of the inserting portion and selects the image pickup adapter to be mounted according to an inspecting target site and an observed purpose and, thereby, it is possible to preferably and easily observe the endoscope image which is desired by the user without the troublesomeness of the participants.

Moreover, the current limiting circuit can be omitted from the image pickup adapter and the image pickup adapter can have a small size and a small diameter and also an excessive current can certainly be prevented from flowing to the image pickup adapter and heating by providing the current limiting circuit in the operating section.

Although, according to the present embodiment, the endoscope is described as an industrial endoscope, the endoscope is not limited to the industrial endoscope and this structure may be applied to a medical endoscope.

The display means is not limited to the CRT monitor and a liquid crystal monitor as an external device may be used.

Further, in the first to sixth embodiments, in place of the battery, an AC adapter may be used.

A seventh embodiment of the present invention will be described with reference to FIGS. 18 to 24.

An electronic endoscope of the present embodiment uses an external power supply in place of the battery as a power supply section and has a first power supply circuit substrate for supplying a power to the C-MOS image sensor and a second power supply circuit substrate for supplying a power to the LED for illumination in an image pickup adapter. Then, according to the present embodiment, the electronic endoscope is described as an industrial endoscope.

Figure 18:
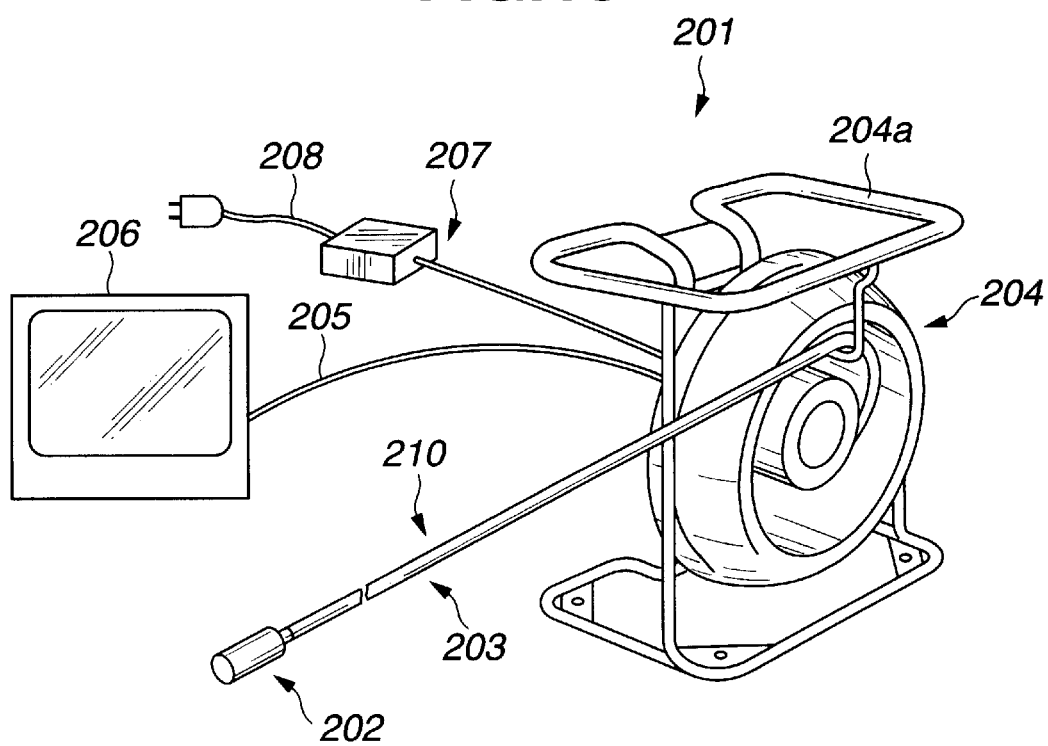

As shown in FIG. 18, an endoscope apparatus 201 according to the present embodiment has an endoscope 210 in which a plurality of kinds of image pickup adapters 202 that are prepared in accordance with an inspecting situation and an inspecting purpose can be detachably arranged at a distal end portion of an inserting portion 203. The inserting portion 203 of the endoscope 210 is wound to a drum 204 and accommodated. A power supply cord 208 having a video cable 205 and a DC power supply adapter 207 extends out from the drum 204. The video cable 205 is connected to a display device 206 such as a CRT monitor and the power supply cord 208 is connected to a power supply plug socket (not shown).

Incidentally, a battery, e.g., a dry cell or a rechargeable battery may be provided in the drum 204.

Figures 19A, 19B:
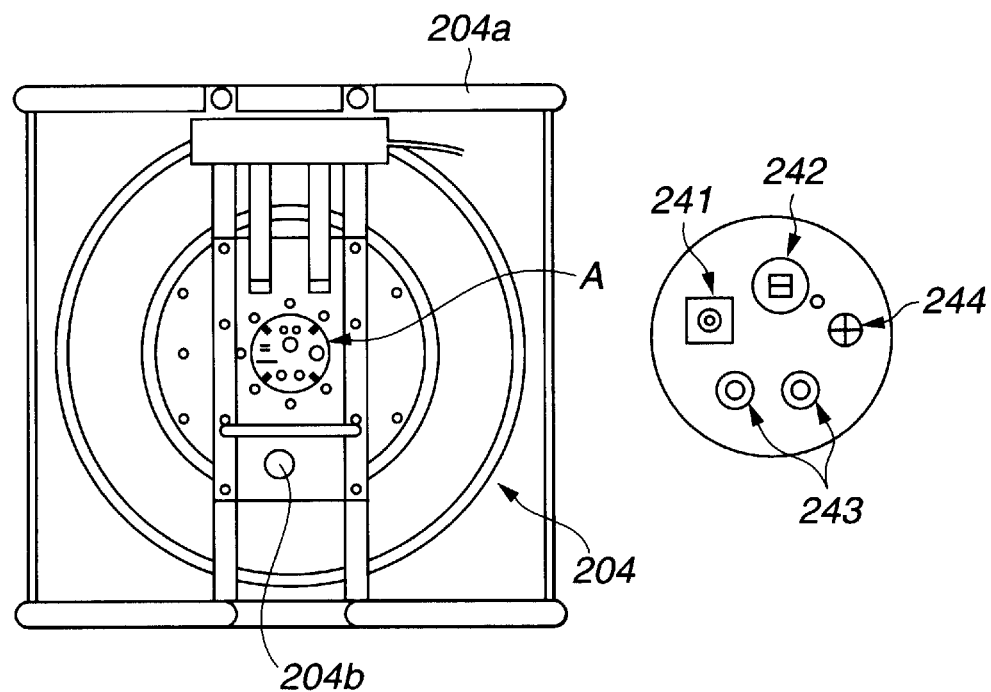
FIG. 19A is a diagram showing the drum and the frame.
FIG. 19B is a diagram for illustrating the main portion of the drum.

As shown in FIGS. 18, 19A, and 19B, the drum 204 is detachably mounted to a frame 204a. A drum stopper 204b which is provided at a predetermined position of the frame 204a is properly operated, thereby setting the drum 204 to be in a rotatable state or stop situation.

A power supply connector 241, a power supply switch 242, a signal output connector 243, and an LED light quantity change-over switch 244 which also functions as temperature increase control means are provided at almost the central portion.

Figure 20:
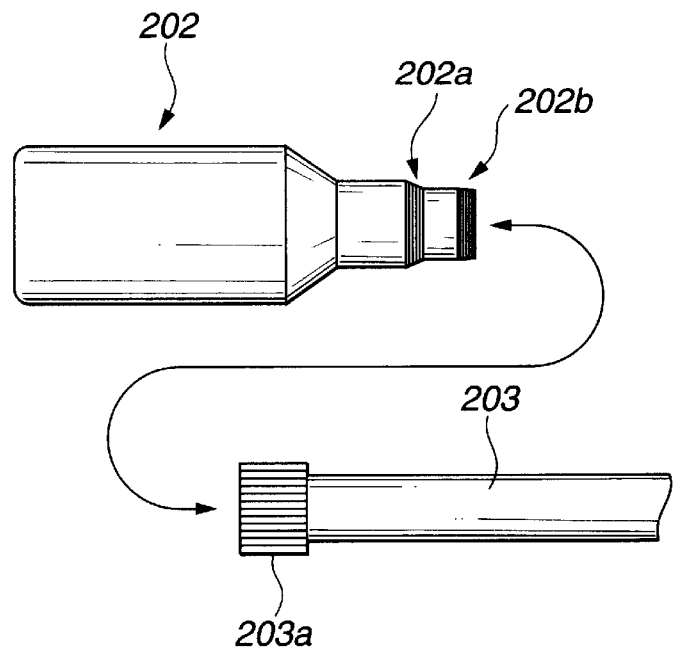

As shown in FIG. 20, two male screw sections 202a and 202b which construct a double screw section as a drop preventing mechanism are formed at a basic end portion of the image pickup adapter 202. A connection fixing member 203a having a female section (not shown) is provided at a distal end portion of the inserting portion 203. Thus, the image pickup adapter 202 in which the male screw sections 202a and 202b are formed is screwed into the distal end portion of the inserting portion 203, thereby being detachably fixed thereto.

Figure 21:
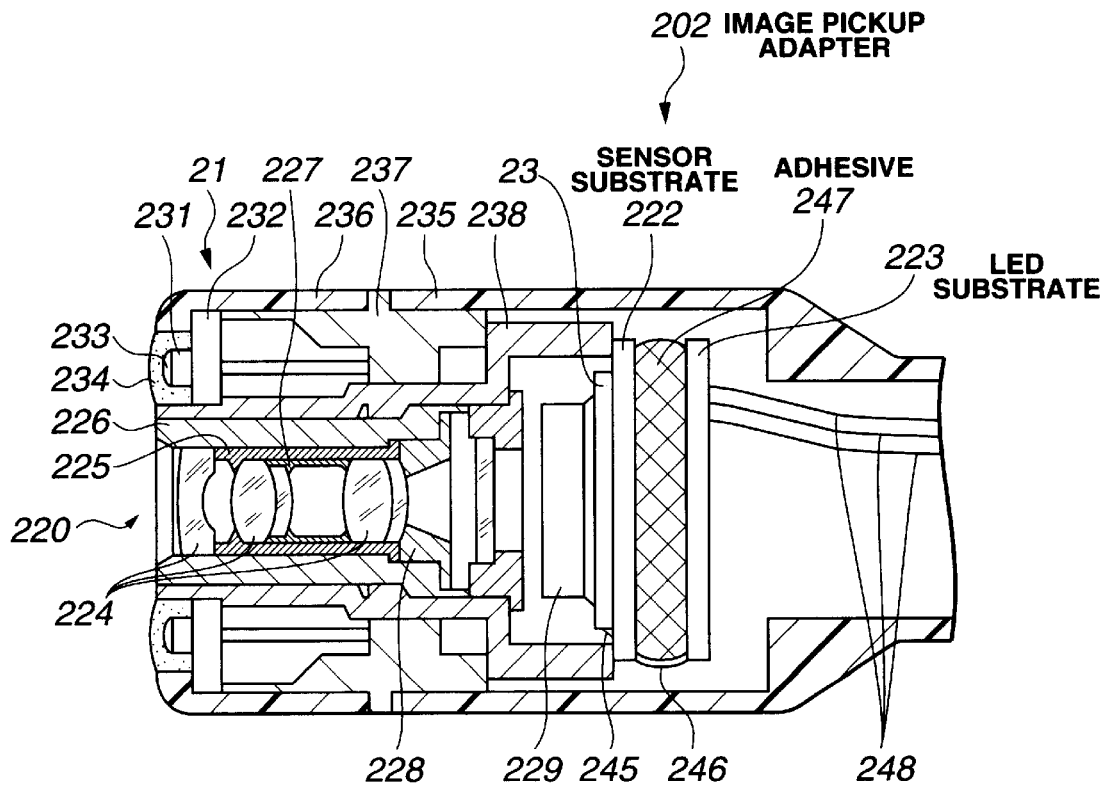

As shown in FIG. 21, an LED chip 231 and a substrate 232 for LED illumination which construct the illuminating section 21, the C-MOS 23, a C-MOS sensor power supply circuit substrate (abbreviated to a sensor substrate, hereinlater) 223 as a substrate for the C-MOS 23 and a first power supply circuit substrate, an LED illumination power supply circuit substrate (abbreviated to an LED substrate, hereinlater) as a substrate for the illuminating section 21 and a second power supply circuit substrate, and an observation optical system 220, etc. are arranged in the image pickup adapter 202.

The armor of the image pickup adapter 202 is mainly constructed by an armoring member main body 235 which is almost cylindrical and a distal-side armoring member 236 which is arranged at the side of a distal end portion of the armoring member main body 235 and is almost cylindrical.

A distal constructing member 237 for arranging the observation optical system 220 and the illuminating section 21 is engaged and arranged in the inside surface of the distal-side armoring member 236. An outside convex portion which is formed at the outside surface at the center in the longitudinal direction of the distal constructing member 237 is sandwiched and arranged between the armoring member main body 235 and the distal-side armoring member 236.

A plurality of optical lenses 224, construct the observation optical system 220 and a sensor casing 238 that is pipe-shaped with steps in which the plurality of optical lenses 224, and the C-MOS 23 are provided at almost the center of the distal constructing member 237.

The observation optical system 220 is constructed by, for example, lens frames 225 and 226 in which the plurality of optical lenses 224 are arranged and interval rings 227 and 228 which set intervals of the adjacent optical lenses 224 in the lens frames 225 to a predetermined value, etc. A male screw section (not shown) is formed on the outside surface of the basic distal end portion of the lens frame 226. The male screw section is screwed to a female screw section (not shown) which is formed at the basic distal end portion of a through-hole of the sensor casing 238.

Therefore, the lens frame 226 moves in the optical axis direction to the sensor casing 238 by rotating the lens frame 226. The position of the lens frame 226 in the optical direction is adjusted and a focal point can accurately be adjusted.

An O-ring and a silicon filler, etc. are provided to a connected surface of the armoring member main body 235, the distal-side armoring member 236, and the distal constructing member 237 and, thus, the image pickup adapter 202 has a water proof structure that water, etc. does not enter to the inside from the connected surface.

A thin silicon material 233 is provided at a surface of the distal end portion of the LED chip 231 of the illuminating section 21. The illuminating section 21 is fixed and arranged at a predetermined position of the distal-side armoring member 236 by filling a transparent adhesive 234 on the silicon material 233. Thus, if a crack, etc. is caused in the adhesive 234, no water enters far the LED chip 231 by providing the silicon material 233.

Figure 22:
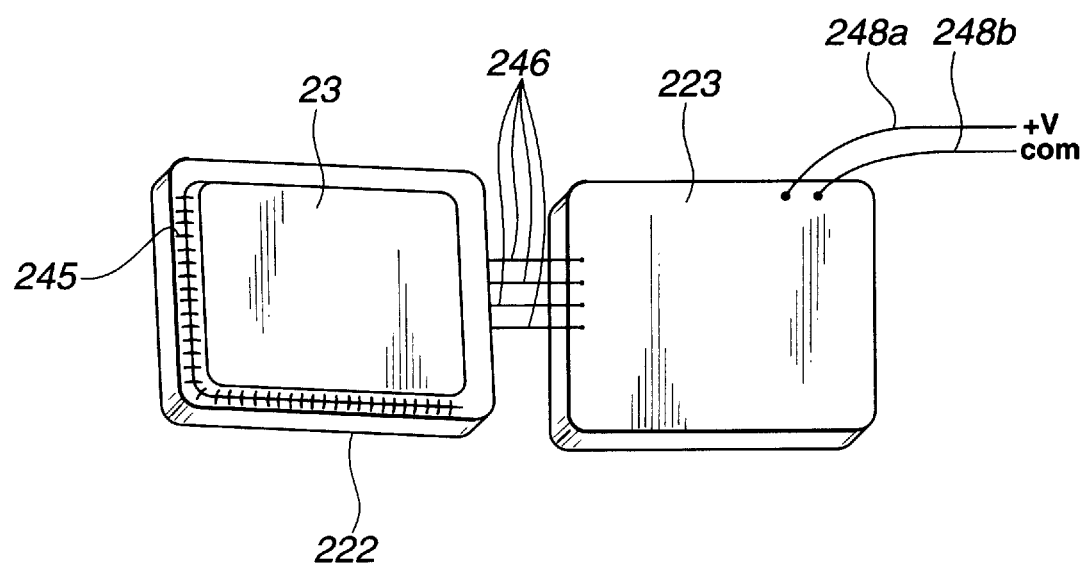

As shown in FIGS. 21 and 22, the C-MOS 23 is electrically connected and fixed to the side of one surface of the sensor substrate 222 by a wiring 245. A transparent casing body 229 is sealed and fixed at the front of an image pickup surface of the C-MOS 23.

The sensor substrate 222 and the LED substrate 223 are members having intensities against tension and torsion, and both thereof are electrically connected by a wiring member 246 which is formed with a predetermined length. The sensor substrate 222 and the LED substrate 223 are integrally fixed by curving the wiring member 246, causing the sensor substrate 222 to face the LED substrate 223, applying, for example, a predetermined amount of epoxy-system adhesive 247 between the substrates 222 and 223 and, thus, providing a space between the sensor substrate 22 and the LED substrate 223, In the sensor substrate 222 and the LED substrate 223 which are integrally fixed, the sensor substrate 222 is positioned and fixed to a surface of the end of the sensor casing 238 by, for instance, adhesion. Thereby, the LED substrate 223 which is connected to the illuminating section 21 and thus generates a large quantity of heat is arranged at the position apart from the C-MOS 23, that is, at the position where it is difficult to conduct heat to the C-MOS 23. Incidentally, reference numerals 248a and 248b denote electric cables for driving which are connected to the LED substrate 223.

Next, the electric connection of an image pickup adapter 202 and an inserting portion 203 will be described with reference to FIG. 23.

As shown in the figure, a distal connector section 209a is provided at the distal end portion of the inserting portion 203. A connector 209b on the adapter side which is detachable to the distal connector section 209a is provided at the basic end portion of the image pickup adapter 202. Cables 203b and 203d for driving and a signal transmission cable 203c are inserted in the inserting portion 203. An electric cables 248a and 248b for driving and a signal transmission cable 248c are inserted in the image pickup adapter 202.

Incidentally, reference numeral 249 denotes an electric cable for illumination via which the LED substrate 223 is electrically connected to the illuminating section 21.

With the aforementioned construction, for example, a power +V and COM which are supplied by connecting the DC power supply adapter 207 to the power supply connector 241 of the drum 204 are supplied to the LED substrate 223 via the cables 203b and 203d for driving, the distal connector section 209a, the connector 209b on the adapter side, and the electric cables 248a and 248b for driving which are inserted in the inserting portion 203.

The power +V and COM which are supplied to the LED substrate 223 are converted into a voltage corresponding to the LED chip 231, are supplied to the illuminating section 21 via the electric cable 249 for illumination, and are supplied to the sensor substrate 222 via the wiring member 246.

Accordingly, illuminating light is irradiated to an observed site from the LED chip 231 of the illuminating section 21, an optical image of the observed site which is irradiated by the illuminating light of the LED chip 231 passes through the observation optical system 220, is formed on the image pickup surface of the C-MOS 23, and is converted into an image signal.

The image signal is inputted to an amplifier 250 via the signal transmission cable 248c, the connector 209b on the adapter side, the distal connector section 209a, and the signal transmission cable 203c, is amplified, is outputted to the display device 206 via the video cable 205 from the signal output connector 243, and an endoscope image is displayed.

Figure 23:
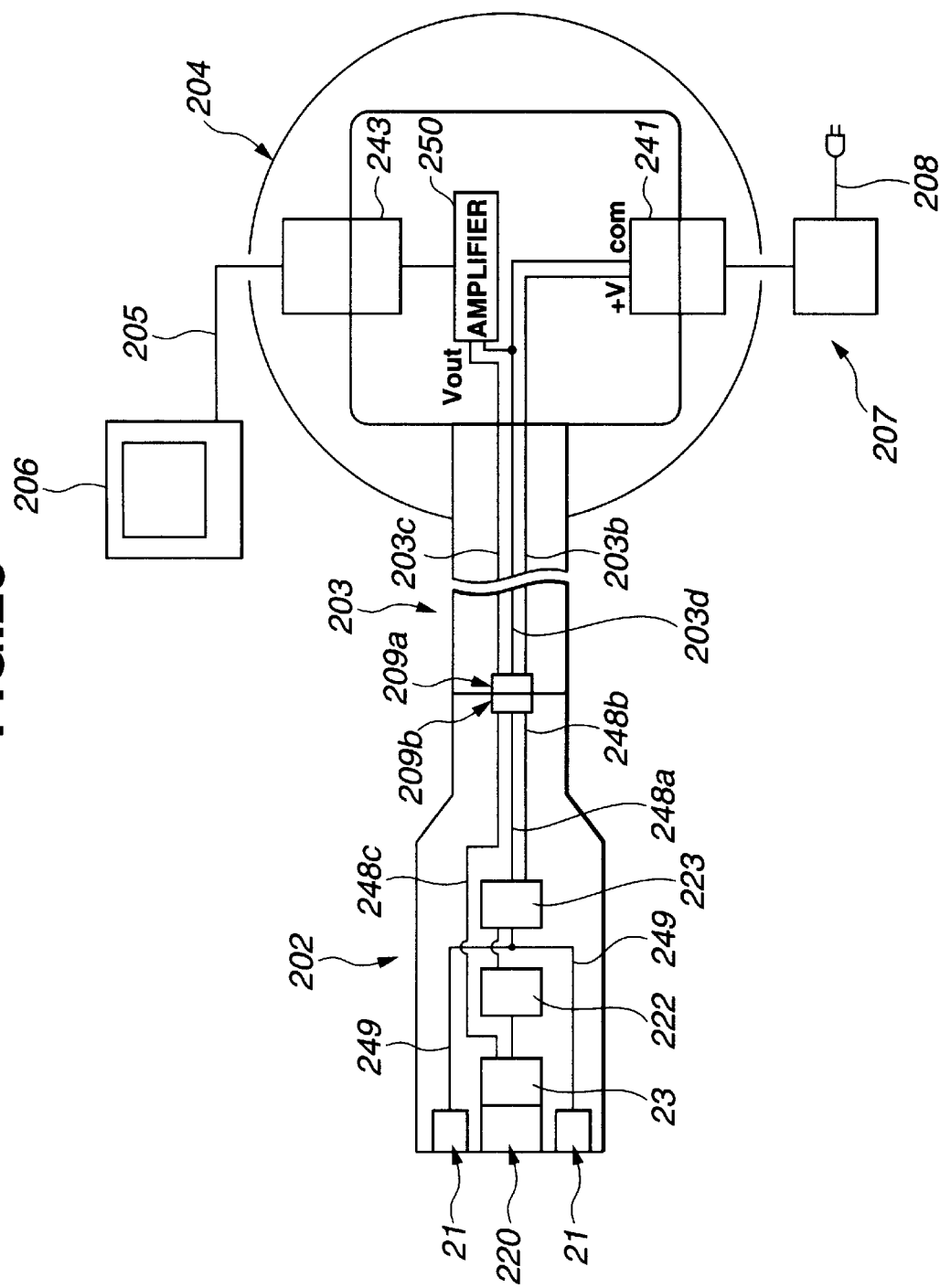
Figure 24A:
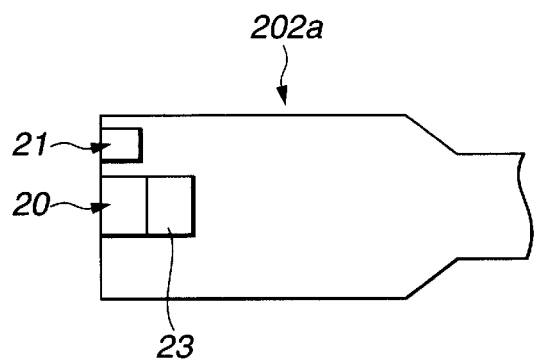
FIG. 24A is a diagram showing still another structure of the image pickup adapter.
Figure 24B:
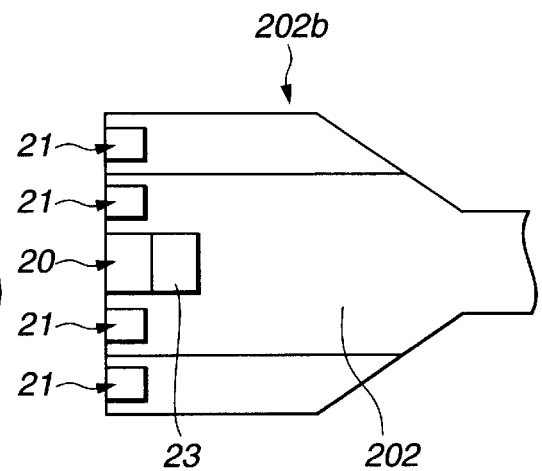
FIG. 24B is a diagram showing yet another structure of the image pickup adapter.

Although, according to the present embodiment, a plurality of illuminating sections 21 which are provided in the image pickup adapter 202 are arranged while sandwiching the observation optical system 220 as shown in FIG. 23, of course, the image pickup adapter 202 is not limited to this construction. For instance, as shown in FIG. 24A, one C-MOS 23 and one illuminating section 21 may be provided in an image pickup adapter 202a. As shown in FIG. 24B, an adapter 202b for LED that is almost pipe-shaped in which a plurality of illuminating sections 21 are provided may be detachably provided as a piping which is large in diameter in the image pickup adapter 202 and double illuminating sections 21 may be arranged, etc.

The operation of the endoscope apparatus 201 with the above-explained construction will be described.

First, a user selects the image pickup adapter 202 in which the C-MOS 23 having the number of pixels or pixel construction according to the diameter and the inspecting purpose of a piping as an observed target is combined with the illuminating section 21, and mounts the selected image pickup adapter 202 in the inserting portion 203. The user also connects the video cable 205 to the display device 206 and the signal output connector 243.

Next, the switch 242 which is provided in the drum 204 is operated and a power is supplied to the C-MOS 23 and the illuminating section 21. Then, a video signal which is outputted from the C-MOS 23 is transmitted to the display device 206, and an endoscope image of the observed site is displayed on the screen.

Incidentally, when the endoscope image which is desired by the user is not obtained, the image pickup adapter 202 is exchanged by another image pickup adapter so that the desired endoscope image can be obtained.

Sequentially, the drum stopper 204b which is provided in the drum 204 is reset and the drum 204 is rotated. The inserting portion 203 of the endoscope 210 is taken out and the image pickup adapter 202 is inserted to the inside of the piping. In this case, when the observed image in the piping is dark, the LED light quantity change-over switch 244 is operated and the quantity of light which is emitted from the LED chip 231 is made light.

If the image pickup adapter 202 is used for long time in the light state, heat which is generated from the LED chip 231 is transmitted to the C-MOS 23, irrespective of that the LED substrate 223 is arranged at the position apart from the C-MOS sensor 23. Then, the temperature of the C-MOS 23 increases and causes noise in the endoscope image. In this case, the LED light quantity change-over switch 244 is operated, the quantity of light which is emitted from the LED chip 231 is decreased, and the quantity of heat which is generated by the LED chip 231 is decreased.

As mentioned above, the C-MOS sensor power supply circuit substrate and the LED illuminating power supply circuit substrate are constructed separately, and the LED illuminating power circuit substrate which dissipates a large quantity of heat is arranged at the position apart from the C-MOS sensor. Thereby, the temperature of the C-MOS sensor can be prevented from increasing by the heat which the LED illuminating power supply circuit substrate dissipates and the occurrence of noises in the endoscope image can be prevented during the observation for long time.

When the heat which is generated by the LED chip of the LED illuminating section causes the temperature of the C-MOS sensor to increase by providing the LED light quantity change-over switch, the quantity of illuminating light of the LED chip is reduced and the temperature of the C-MOS sensor can be prevented from increasing excessively and the occurrence of noises in the endoscope image can be prevented.

Accordingly, the endoscope image having a preferable image quality can be obtained, so that the observing performance is largely improved.

Figure 25:
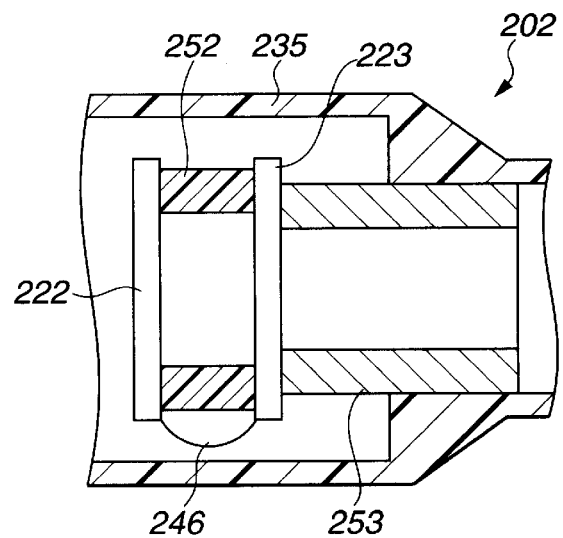
FIG. 25 is a diagram illustrating another structure in that the C-MOS sensor power supply circuit substrate and an LED illuminating power supply circuit substrate are integrated.

Although, as shown in FIG. 25, a member having a low thermal conductivity, in other words, a foaming resin 252 which is made of polystyrene and urethane in the form of a column which insulates heat may be provided between the sensor substrate 222 and the LED substrate 223. A metallic member 253 having a high thermal-conductivity may be provided at the side of the LED substrate 223 and the metallic member 253 may come into contact with the armoring member main body 235, thereby dissipating heat to the outside.

Figure 26:
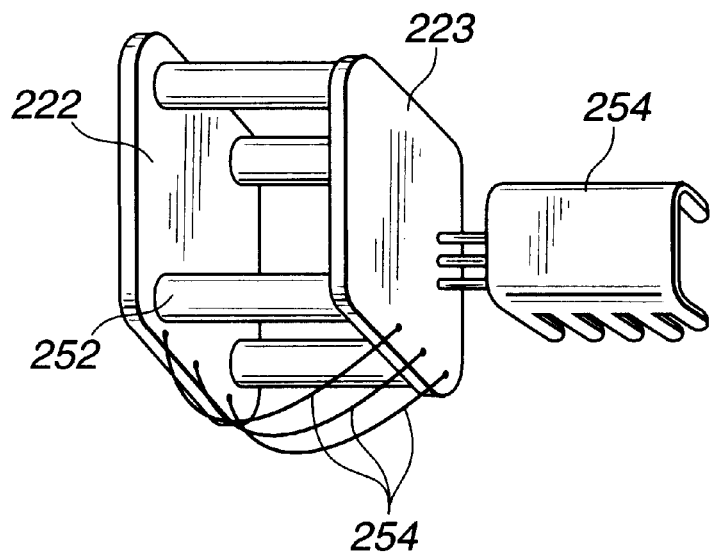
FIG. 26 is a diagram illustrating still another structure in that the C-MOS sensor power supply circuit substrate and the LED illuminating power supply circuit substrate are integrated.

The foaming resin 252 may be arranged between the sensor substrate 222 and the LED substrate 223 as shown in FIG. 26. A heat sink 254 may be also provided at either one or both of the sensor substrate 222 and the LED substrate 223.

As explained above, the heat of the LED illuminating power supply circuit substrate is dissipated to the outside, so that the increase in the temperature of the C-MOS sensor is suppressed at the minimum level and the similar operation and advantage can be obtained.

Further, a Peltier element is provide at the portion of the adhesive 247 shown in FIG. 21 and the sensor substrate 222 is located at the side of cooling. Thereby, the side of the C-MOS sensor can be cooled. In this case, the heat dissipating plate 254 is provided and heat of the LE substrate 223 is dissipated, so that the increase in the temperature of the C-MOS 23 can further be suppressed efficiently.

Figure 27:
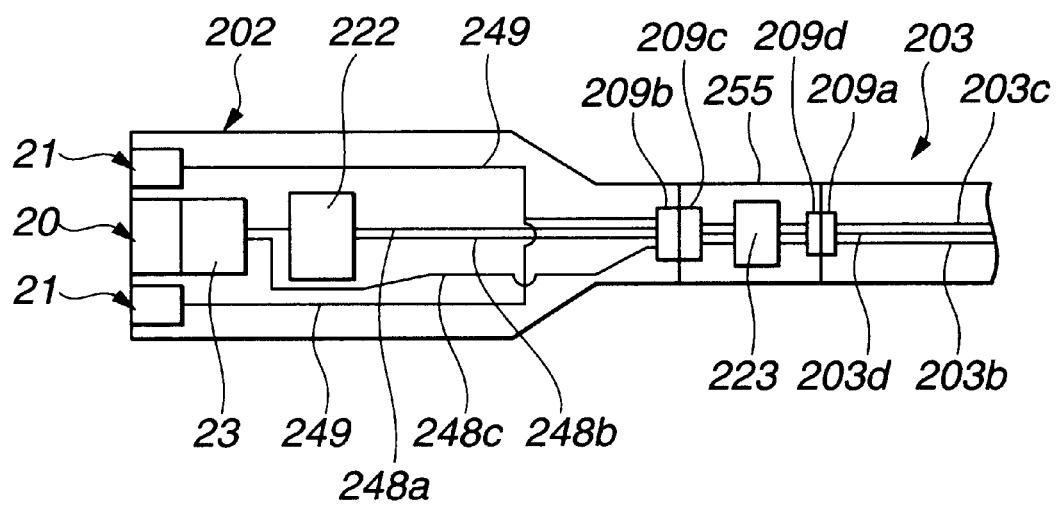
FIG. 27 is a diagram illustrating another structure of the image pickup adapter and the distal end portion of the inserting portion.

As shown in FIG. 27, the LED substrate 223 is built in between the image pickup adapter 202 and the inserting portion 203 and a coupling member 255 having connecting sections 209c and 209d which connects the image pickup adapter 202 to the inserting portion 203 is detachably provided. Thereby, the LED substrate 223 is arranged at the position further apart from the C-MOS 23. Consequently, the temperature of the C-MOS 23 can be prevented from increasing due to the heat of the LED substrate 223.

Incidentally, in place of the coupling member 255, the LED substrate 223 may be arranged at the distal end portion of the inserting portion 203 and may be arranged at the position apart from the C-MOS 23.

Figure 28:
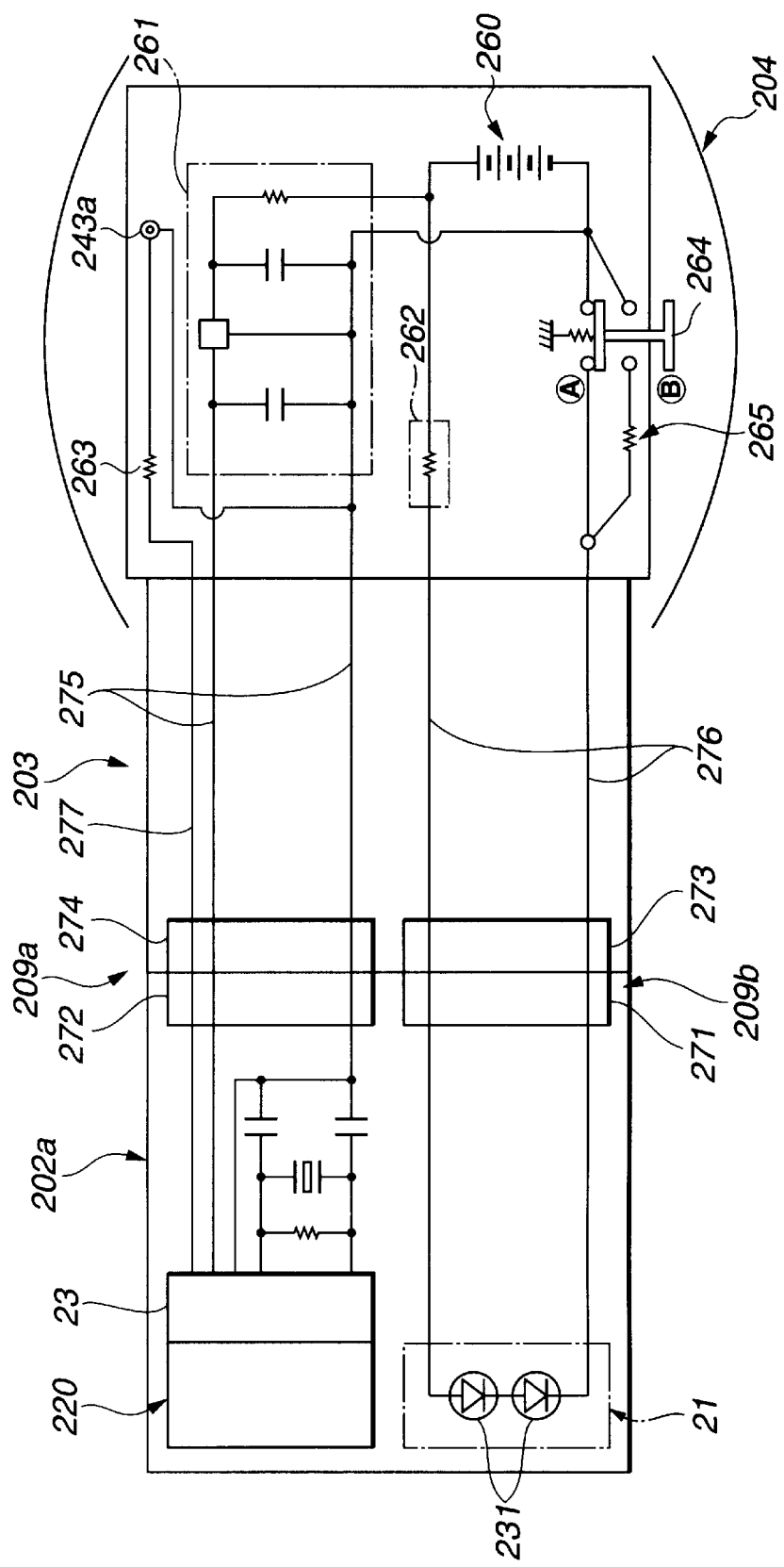
FIG. 28 is a diagram illustrating one specific structure of a light quantity change-over switch as light quantity switching means.

FIG. 28 is a diagram for illustrating a specific structure of the light quantity change-over switch as light quantity switching means.

As shown in the figure, an LED connecting section 271 on the adapter side and a sensor connecting section 272 on the adapter side are provided to the connector 209b on the adapter side which is provided at the surface of the basic end of the image pickup adapter 202a according to the present embodiment.

An LED connecting section 273 on the inserting portion side and a sensor connecting section 274 on the inserting portion which are electrically connected to the LED connecting section 271 on the adapter side and the sensor connecting section 272 on the adapter side, respectively, are provided to the distal connector section 209a on the surface of the distal end portion of the inserting portion 203 of the endoscope 210.

The connecting sections 273 and 274 of the distal connector section 209a are made electrically conductive to the connecting sections 271 and 273 of the connector 209b on the adapter side by connecting the connector 209b on the adapter side to the distal connector section 209a.

A driving cable 275 which electrically connects the connecting section 274 on the inserting portion side to a battery 260 as a power supply section that is provided in the drum 204 and supplies a driving power to the C-MOS 23, a cable 276 for illumination which electrically connects the LED connecting section 273 on the inserting portion side to the battery 260 and supplies a power for illumination to one or a plurality of LED chips 231 that construct the illuminating section 21, a signal transmission cable 277 which extends from the sensor connecting section 274 on the inserting portion side and transmits a video signal that is generated by the C-MOS 23 to a video signal output terminal section, which will be described later on, are inserted in the inserting portion 203.

A constant voltage circuit 261 which stabilizes a power to be supplied to the C-MOS 23 and a power supply limiting circuit 262 which is located at the intermediate position of the cable 276 for illumination via which the battery 260 is connected to the illuminating section 21 and limits a value of a current that is supplied to the illuminating section 21 are provided in the drum 204.

A video output terminal section 243a as the signal output connector 243 which is detachably connected to the video cable 205 for transmitting the video signal that is outputted from the C-MOS 23 to the display device 206 is provided at, for instance, the end portion of the drum 204. The signal transmission cable 277 is electrically connected to the video output terminal section 243a via a resistor 263.

Reference numeral 264 denotes an LED light quantity change-over switch (abbreviated to a switch, hereinafter) which also functions as temperature increase control means. The switch 264 is a change-over switch of a pressing button type which is switched and arranged at the position shown by, e.g., a symbol A or at the position shown by, e.g. a symbol B by pressing operation.

Therefore, the switch 264 is switched and is arranged at the position shown by symbol B at which the resistor 265 is provided or at the position shown by symbol A at which the resistor 265 is not provided by operating the switch 264, so that the quantity of illuminating light which is irradiated from the illuminating section 21 can be changed.

As described above, the LED light quantity change-over switch is provided and the quantity of illuminating light is switched step by step. Therefore, an user selects the quantity of light which is emitted from the LED illuminating section in consideration of the size of piping and reduces the quantity of light when noises occur in the endoscope image. Accordingly, a preferable endoscope image can be observed.

Figure 29A:
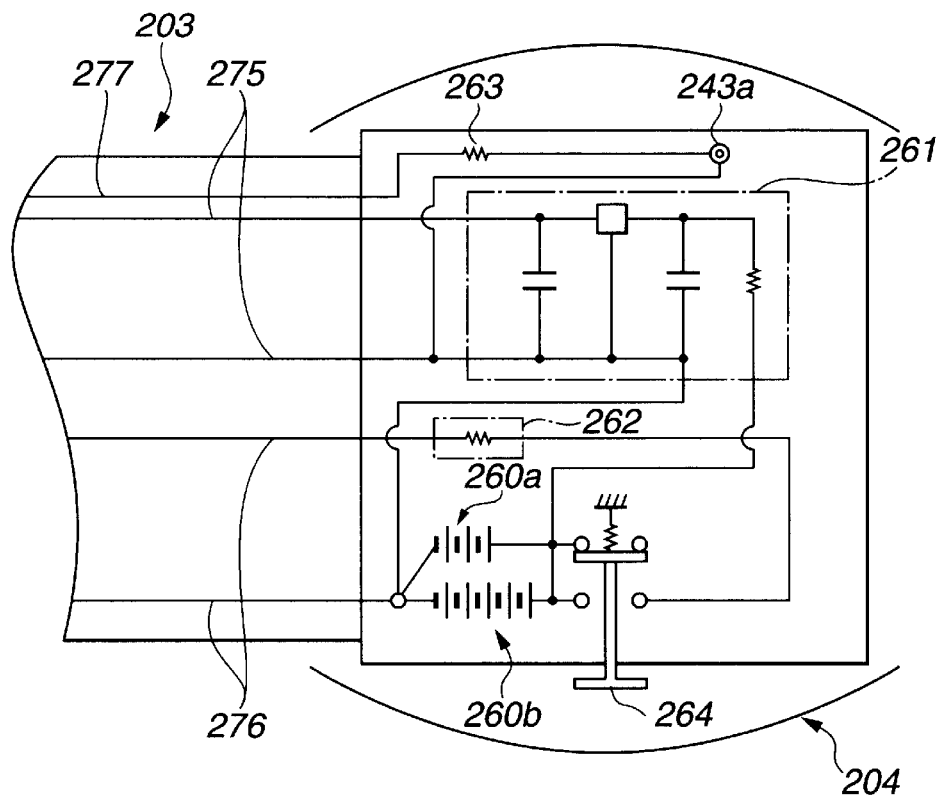
FIG. 29A is a diagram illustrating still another structure of the light quantity change-over switch.

Although, according to the present embodiment, the switch is operated by switching at two steps, the switch is not limited to the switching at two steps and the number of switching steps may be set to be two or more. As shown in FIG. 29, for example, two battery sections of battery sections 260a and 260b which have different voltage values may be provided, and a power to be supplied to the illuminating section 21 may be switched to the battery section 260a or the battery section 260b by operating the switch 264.

Figure 29B:
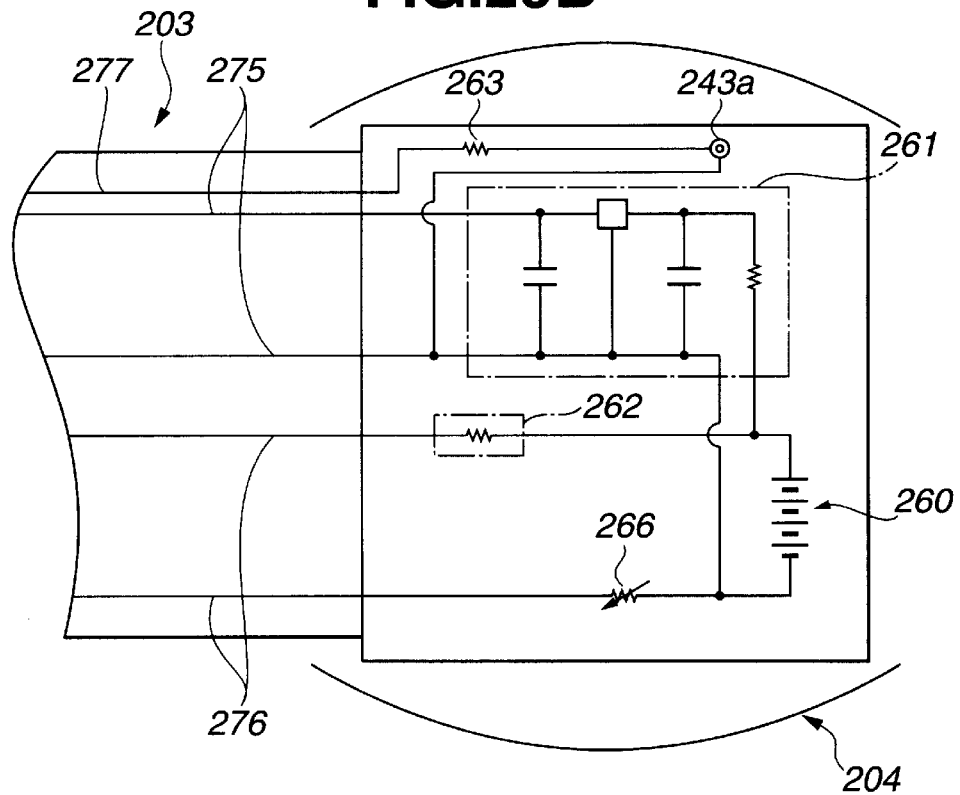
FIG. 29B is a diagram illustrating yet still another structure of the light quantity change-over switch.

Further, in place of using the LED light quantity change-over switch of the pressing button type, a variable resistor 266 may be provided as shown in FIG. 29B. As for the variable resistor 266, there are one of a type that a resistance changes by rotating a knob, and one of a type that a resistance changes by slide-moving a knob, etc. Thus, the quantity of light is changed not by step by step but sequentially and, then, the quantity of light can be finely adjusted in accordance with the size of the piping, etc.

According to the present invention, it will be apparent to one skilled without departing from the spirit and scope of the present invention.

What is claimed is:

1. An electronic endoscope, comprising:
   an operating portion;
   an inserting portion coupled to the operating portion and arranged distally thereof; and
   an image pickup adapter detachably coupleable to an end of the inserting portion, the image pickup adapter including at least one LED to emit light to illuminate an observed site; a C-MOS image sensor having an image pickup surface on which an optical image of the observed site is formed, the C-MOS image sensor outputting a video signal to the operating section, the video signal corresponding to the optical image; a first power supply circuit substrate which supplies power to the C-MOS image sensor; a second power supply circuit substrate which supplies power to the at least one LED; and a temperature increase controller which prevents an increase in temperature of the C-MOS image sensor above a predetermined temperature.

2. An electronic endoscope according to claim 1, wherein the temperature increase controller is arranged between the first power supply circuit substrate and the second power supply circuit substrate.

3. An electronic endoscope according to claim 1, further comprising: a member having a low thermal conductivity arranged between the first power supply circuit substrate and the second power supply circuit substrate.

4. An electronic endoscope according to claim 1, wherein the temperature increase controller is a heat sink which is provided for at least one of the first power supply circuit substrate and the second power supply circuit substrate.

5. An electronic endoscope according to claim 1, further comprising:
   wherein the inserting portion having an end portion is such that the image pickup adapter is attachable and detachable therefrom, the inserting portion further having an electric cable which is electrically connected to the C-MOS image sensor and the at least one LED when the image pickup adapter is attached to the inserting portion.

6. An electronic endoscope according to claim 1, wherein the endoscope has a drum to which the insertion portion is wound.

7. An electronic endoscope according to claim 6, wherein the temperature increase controller is provided adjacent a central portion of the drum.

8. An electronic endoscope according to claim 1, including silicon material provided at a surface of a distal end portion of the LED.

9. An electronic endoscope according to claim 1, wherein the first power supply circuit substrate and the second power supply circuit substrate are located to face each other.

10. An electronic endoscope according to claim 1, wherein the adapter is generally pipe-shaped in which a plurality of LEDs are provided.

11. An electronic endoscope according to claim 1, wherein a member having a low thermal conductivity is provided between the first power supply circuit substrate and the second power supply circuit substrate, and a metallic member having a high thermal-conductivity is provided at a side of the second power supply circuit substrate and this metallic member contacts an armoring member main body.

12. An electronic endoscope according to claim 1, wherein the second power supply circuit substrate is located between the image pickup adapter and the inserting portion and a coupling member is detachably provided.

13. An electronic endoscope, comprising:

an operating portion;

an inserting portion coupled to the operating portion and arranged distally thereof; and an image pickup adapter detachably coupleable to an end of the inserting portion, the image pickup adapter including at least one LED to emit light to illuminate an observed site; a C-MOS image sensor having an image pickup surface on which an optical image of the observed site is formed, the C-MOS image sensor outputting a video signal to the operating section, the video signal corresponding to the optical image; a first power supply circuit substrate to supply power to the C-MOS image sensor; a second power supply circuit substrate to supply power to the at least one LED; and a temperature increase controller to prevent an increase in temperature of the C-MOS image sensor above a predetermined temperature, wherein the temperature increase controller is a light quantity switch which changes a quantity of light emitted by the illuminating section.

14. An electronic endoscope according to claim 13, wherein the light quantity switch varies a resistance by a rotating or sliding operation and controls a voltage which flows to the illuminating section from the second power supply circuit substrate.

15. An electronic endoscope according to claim 13, further comprising: a plurality of power sources connected between the illuminating section and the light quantity switch, wherein the light quantity switch is operable to select a power source from the plurality of power sources which is to supply power to the illuminating section.

* * * * *